United States Patent
Landschütze

(10) Patent No.: US 7,247,769 B2
(45) Date of Patent: *Jul. 24, 2007

(54) PLANTS SYNTHESIZING A MODIFIED STARCH, A PROCESS FOR THE GENERATION OF THE PLANTS, THEIR USE, AND THE MODIFIED STARCH

(75) Inventor: Volker Landschütze, Berlin (DE)

(73) Assignee: Bayer CropScience GmbH, Frankfurt (DE)

(*) Notice: Subject to any disclaimer, the term of this patent is extended or adjusted under 35 U.S.C. 154(b) by 410 days.

This patent is subject to a terminal disclaimer.

(21) Appl. No.: 10/424,799

(22) Filed: Apr. 28, 2003

(65) Prior Publication Data

US 2003/0167529 A1 Sep. 4, 2003

Related U.S. Application Data

(63) Continuation of application No. 09/364,185, filed on Jul. 29, 1999, now Pat. No. 6,596,928.

(30) Foreign Application Priority Data

Jul. 31, 1998 (DE) .................. 198 36 098

(51) Int. Cl.
*C12N 15/82* (2006.01)
*C12N 5/04* (2006.01)
*A01H 5/00* (2006.01)
*A01H 5/10* (2006.01)
*C12P 19/00* (2006.01)

(52) U.S. Cl. ............ 800/284; 800/286; 800/317.2; 435/320.1; 435/417; 435/419

(58) Field of Classification Search .......... 536/23.2, 536/23.6, 24.5; 435/101, 320.1, 417, 429; 800/284, 278, 286, 317.2

See application file for complete search history.

(56) References Cited

U.S. PATENT DOCUMENTS

| | | | |
|---|---|---|---|
| 4,962,028 A | 10/1990 | Bedbrook et al. | |
| 5,034,322 A | 7/1991 | Rogers et al. | |
| 5,639,952 A | 6/1997 | Quail et al. | |
| 5,656,496 A | 8/1997 | Quail et al. | |
| 6,596,928 B1 | 7/2003 | Landschütze | |

FOREIGN PATENT DOCUMENTS

| | | |
|---|---|---|
| CA | 2231774 | 3/1998 |
| DE | 196 36 917 | 3/1998 |
| EP | 0 120 516 | 10/1984 |
| EP | 0 292 435 | 11/1988 |
| EP | 0 321 201 | 6/1989 |
| EP | 0 368 506 | 5/1990 |
| EP | 0 455 316 | 11/1991 |
| EP | 0 465 875 | 1/1992 |
| EP | 0 513 849 | 11/1992 |
| EP | 0 779 363 | 6/1997 |
| EP | 458367 | * 10/2001 |
| WO | WO 92/11375 | 7/1992 |
| WO | WO 92/11376 | 7/1992 |
| WO | WO 92/11382 | 7/1992 |
| WO | WO 92/14827 | 9/1992 |
| WO | WO 94/09144 | 4/1994 |
| WO | WO 94/11520 | 5/1994 |
| WO | WO 94/28146 | 12/1994 |
| WO | WO 95/06128 | 3/1995 |
| WO | WO 95/07335 | 3/1995 |
| WO | WO 95/09922 | 4/1995 |
| WO | WO 95/15972 | 6/1995 |
| WO | WO 95/26407 | 10/1995 |
| WO | WO 96/15248 | 5/1996 |
| WO | WO 96/19581 | 6/1996 |
| WO | WO 97/11188 | 3/1997 |
| WO | WO 97/20040 | 6/1997 |
| WO | WO 97/20936 | 6/1997 |
| WO | WO 97/22703 | 6/1997 |
| WO | WO 97/26362 | 7/1997 |
| WO | WO 97/32985 | 9/1997 |
| WO | WO 97/42328 | 11/1997 |
| WO | WO 97/44472 | 11/1997 |
| WO | WO 97/45545 | 12/1997 |
| WO | WO 98/22604 | 5/1998 |
| WO | WO 98/44780 | 10/1998 |
| WO | WO 99/66050 | 12/1999 |

OTHER PUBLICATIONS

Edwards et al. The Plant Journal 17(3): 251-261 (1999).*
Stam et al. Annals of Botany 79: 3-12 (1997).*
Colliver et al. Plant Molecular Biology 35: 509-522 (1997).*
Kossman et al. pp. 271-278 In: Carbohydrate Bioengineering, Petersen et al, eds, Elsevier Science: Amsterdam (1995).*
Rothstein et al. PNAS 84: 8439-8443 (Dec. 1987).*
Rodermel et al. Cell 55: 673-681 (Nov. 1988).*
Smith et al. Nature 334: 724-726 (Aug. 1988).*
Cannon et al. Plant Molecular Biology 15: 39-47 (1990).*
Goring et al. PNAS 88: 1770-1774 (Mar. 1991).*
Neuhaus et al. Plant Molecular Biology 19: 803-813 (1992).*
Seymour et al. Plant Molecular Biology 23: 1-9 (1993).*
Estruch et al. PNAS 91: 8837-8841 (Sep. 19994).*
Ni et al. Transgenic Research 3: 120-126 (1994).*

(Continued)

*Primary Examiner*—David T. Fox
(74) *Attorney, Agent, or Firm*—Hunton & Williams LLP

(57) ABSTRACT

The present invention relates to recombinant nucleic acid molecules which contain two or more nucleotide sequences which encode enzymes which participate in the starch metabolism, methods for generating transgenic plant cells and plants which synthesize starch which is modified with regard to its phosphate content and its side-chain structure. The present invention furthermore relates to vectors and host cells which contain the nucleic acid molecules according to the invention, the plant cells and plants which originate from the methods according to the invention, to the starch synthesized by the plant cells and plants according to the invention, and to processes for the preparation of this starch.

23 Claims, 3 Drawing Sheets

OTHER PUBLICATIONS

Dwivedi et al. Plant Molecular Biology 26: 61-71 (1994).*
Xu et al. PNAS 92: 2106-2110 (Mar. 1995).*
Fan et al. The Plant Cell 9: 2183-2196 (Dec. 1997).*
Orvar et al. The Plant Journal 11(6): 1297-1305 (1997).*
Ref. 127:261734, 1997 (Chemical Abstract)., Kossman et al.
Ref. 126:168218, 1996 (Chemical Abstract)., Abel et al.
Nelson and Rines, Biochem. Biophys. Res. Commun. 9, (1962), 297-300.
Villareal and Juliano, Starch/Staerke 38, (1986), 118-119.
Rohde et al., Nucleic Acid Res. 16, (1988), 7185-7186.
Nakamura et al., Mol. Gen. Genet. 248, (1995), 253-259.
Hovenkamp-Hermelink et al., (Theor. Appl. Genet. 75, (1987), 217-221.
Okuno and Sakaguchi, J. Hered. 73, (1982), 467.
Denyer et al., Plant Cell Environ. 18, (1995), 1019-1026.
Delrue et al., J. Bacteriol. 174, (1992), 3612-3620.
Visser et al., Mol. Gen. Genet. 225, (1991), 289-296.
Shimada et al., Theor. Appl. Genet. 86, (1993), 665-672.
Hseih, Bot. Bull. Acad. Sinica 29, (1988), 293-299.
Abel et al., The Plant Journal (1996), 10(6), pp. 981-991.
Lloyd et al., Biochem Journal (1999), 338, pp. 515-521.
Ames (1996) Methods in Enzymology VIII, 115-118.
Abel et al. (1996) Plant J. 10(6):981-991.
An et al. (1985) EMBO J. 4:277-287.
Bansal et al. (1992) Proc. Natl. Acad. Sci USA 89: 3654-3658.
Bimboim & Doly (1979) Nucleic acids Res. 7: 1513-1523.
Braun et al. (1992) EMBO J. 11: 3219-3227.
Buchner et al. (1996) Planta 199:64-73.
Camirand et al. (1989) Plant Physiol. 89(4): 61.
Chan et al. (1993) Plant Mol. Biol. 22: 491-506.
Cole-Strauss et al. (1996) Science 273: 1386-1389.
de Borne et al. (1994) Mol. Gen. Genet. 243: 613-621.
Denyer & Smith (1992) Planta 186: 609-617.
Denyer et al. (1996) Planta 196: 256-265.
Dixon and Arntzen, meeting report on "Metabolic Engineering in Transgenic Plants", Keystone Symposia, Copper Mountain, CO, USA TIBTECH 15 (1997), 441-447.
Dry et. al. (1992) The Plant Journal 2: 193-202.
EMBL (1991) database entry X58453.
EMBL (1993) database entry X74160.
EMBL (1995) database entry X88789.
EMBL (1995) database entry X83969.
Feyter et al. (1996) Mol. Gen. Genet. 250: 329-338.
Flavell et al. (1995) Curr. Top. Microbiol. Immunol. 197: 43-46.
Gielen et al. (1989) EMBO J. 8: 23-29.
Hiei et al. (1994) Plant J. 6: 271-282.
Hizukuri (1986) Carbohydr. Res. 147:342-347.
Höfgen & Willmitzer (1988) Nucleic Acids Res. 16: 9877.
Höfgen & Willmitzer (1990) Plant Sci. 66: 221-230.
Holsters et al. (1978) Mol. Gen. Genet. 163: 181-187.
Koßmann et al. (1991) Mol. & Gen. Genetics 230(1-2): 39-44.
Kren et al. (1997) Hepatology 25: 1462-1468.
Leisy et al. (1990) Plant Mol. Biol. 14: 41-50.
Lin et al. (1991) Plant Physiol. 95: 1250-1253.
McCormick et al. (1986) Plant Cell Reports 5: 81-84.
Murashige & Skoog (1962) Physiol. Plant 15:473.
Nakatani et al. (1992) Japanese J. Crop. Sci. 61(3): 463-468.
Niebel et al. (1995) Curr. Top. Microbiol. Immunol. 197: 91-103.
Nielsen et. al. (1994) Plant Physiol. 105: 111-117.
Palaqui and Vaucheret (1995) Plant. Mol. Biol. 29: 149-159.
Pedersen et al. (1982) Cell 29: 1015-1026.
Prioli and Söndahl (1989) Bio/Technology 7: 589.
Quatroccio et al. (1991) Plant Mol. Biol. 15: 81-93.
Rocha-Sosa et al. (1989) EMBO J. 8: 23-29.
Sonnewald et al. (1991) Plant J. 95-106.
Sonnewald et al. (1995) Plant Mol. Biol. 24:567-576.
Stockhaus et al. (1987) Proc. Natl. Acad. Sci USA 84: 7943-7947.
Stockhaus et al. (1989) EMBO J. 8: 244-2451.
Takaha et al. (1993) J. Biol. Chem. 268: 1391-1396.
Tomlinson et al. (1997) Plant J. 11:31-47.
van der Leij et al. (1991) Mol. Gen Genet. 228:240-248.
Vaucheret et al. (1995) Mol. Gen. Genet. 248: 311-317.
Werr et al. (1985) EMBO J. 4: 1373-1380.
Wolter et al. (1988) Proc. Natl. Acad Sci USA 85: 846-850.
Yoshihara et al. (1996) FEBS Lett. 383: 213-218.
Zheng et al. (1993) Plant J. 4: 357-366.
Shillito, et al., "Regeneration of Fertile Plants from Protoplasts of Elite Inbred Maize", Bio/Technology, vol. 7, p. 581-587, Jun. 1989.

* cited by examiner

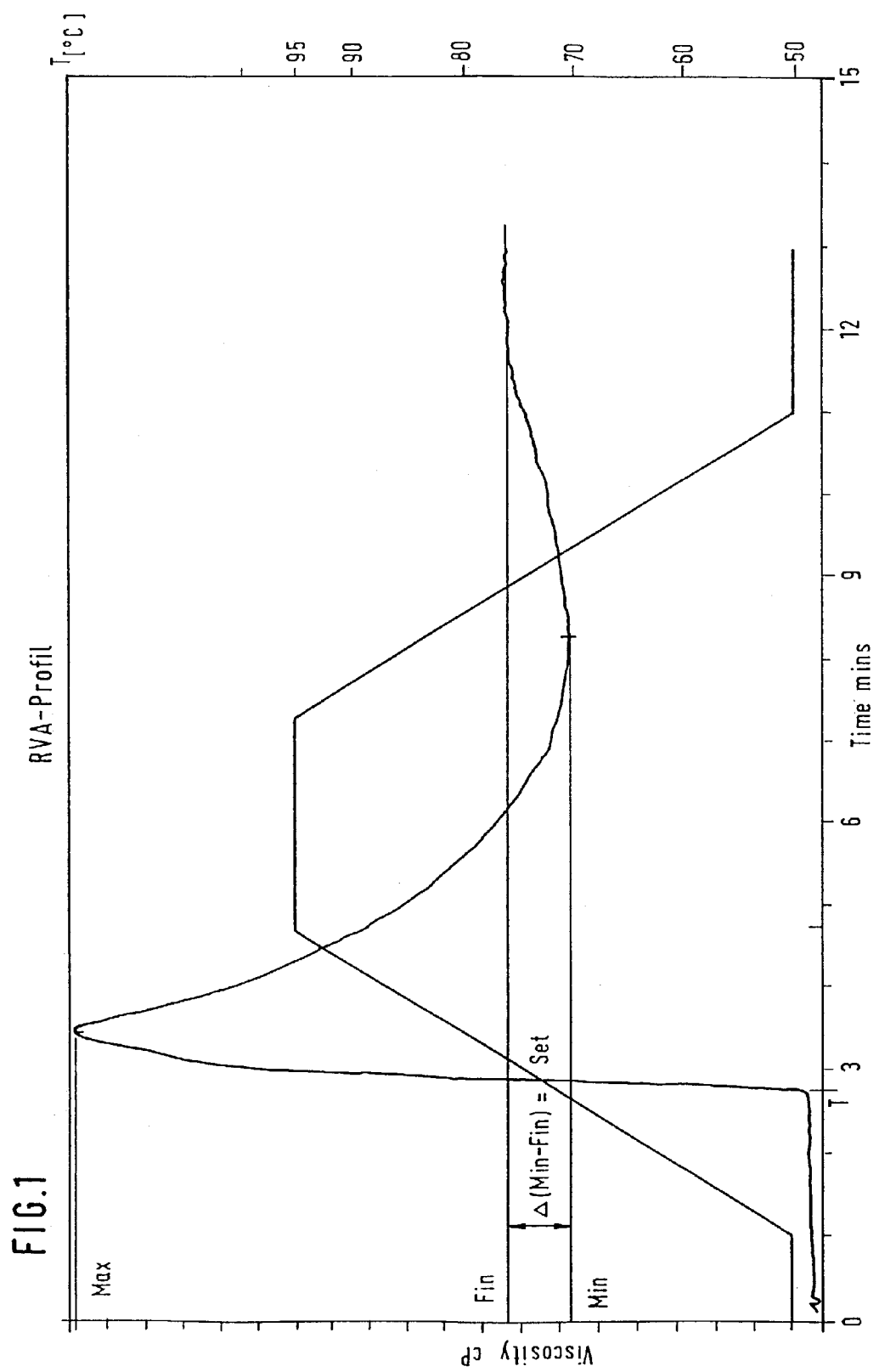

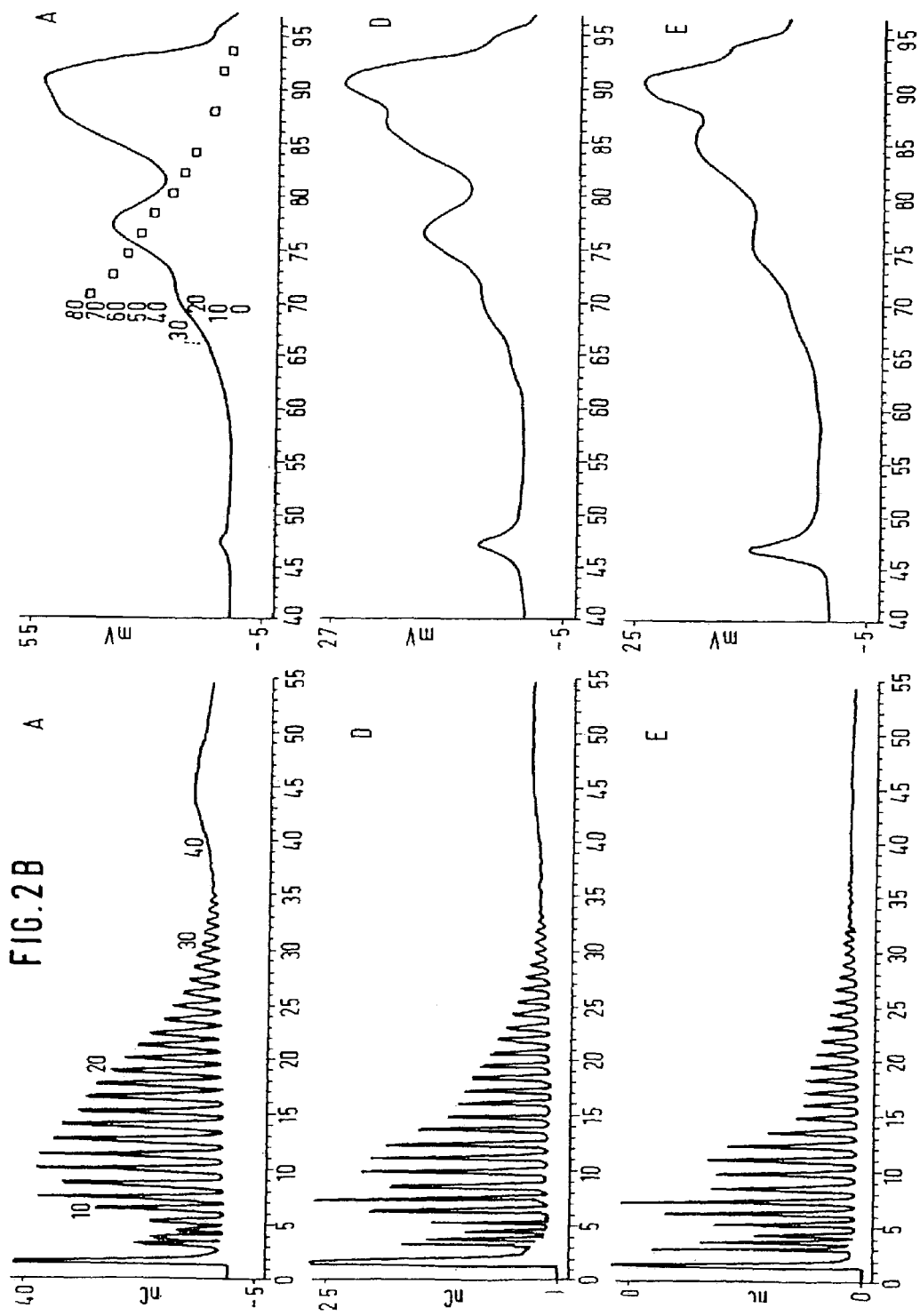

US 7,247,769 B2

PLANTS SYNTHESIZING A MODIFIED STARCH, A PROCESS FOR THE GENERATION OF THE PLANTS, THEIR USE, AND THE MODIFIED STARCH

RELATED APPLICATIONS

This application is a continuation application of U.S. application Ser. No. 09/364,185, filed Jul. 29, 1999, now U.S. Pat. No. 6,596,928, which claims priority from German application 19836098.3, filed Jul. 31, 1998. Each of the foregoing applications, each document cited or referenced in each of the foregoing applications and during the prosecution of each of the foregoing applications ("application cited documents"), each document referenced or cited in each of the application cited documents, each document cited or referenced in this application ("herein cited documents") and each document cited or referenced in each of the herein cited documents are all incorporated herein by reference.

FIELD OF THE INVENTION

The present invention relates to recombinant nucleic acid molecules which comprise two or more nucleotide sequences which encode enzymes which participate in the starch metabolism, to processes for generating transgenic plant cells, and plants which synthesize starch which is modified with regard to their phosphate content and their side-chain structure. The present invention furthermore relates to vectors and host cells which contain the nucleic acid molecules according to the invention, the plant cells and plants which originate from the processes according to the invention, to the starch synthesized by the plant cells and plants according to the invention, and to processes for the preparation of this starch.

BACKGROUND OF THE INVENTION

Bearing in mind the increasing importance of plant constituents as renewable resources, biotechnology research attempts to adapt plant raw materials to the demands of the processing industry. Thus, to make possible the use of renewable resources in as many fields of application as possible, it is necessary to make available a great variety of materials.

Not only oils, fats and proteins, but also polysaccharides, constitute important renewable resources from plants. A pivotal position in the polysaccharides is taken up not only by cellulose, but also by starch, which is one of the most important storage substances in higher plants. Not only corn, rice and wheat, but also potato, plays an important role, in particular in starch production.

The polysaccharide starch is a polymer of chemically uniform units, the glucose molecules. However, it is of a highly complex mixture of different forms of molecules which differ with regard to their degree of polymerization and the occurrence of branchings in the glucose chains. Starch is therefore no uniform raw material. In particular, we differentiate between amylose starch, an essentially unbranched polymer of α-1,4-glycosidically linked glucose molecules, and amylopectin starch which, in turn, constitutes a complex mixture of differently branched glucose chains. Other branchings are generated by the occurrence of additional α-1,6-glycosidic linkages. In typical plants used for starch production such as, for example, corn or potatoes, the synthesized starch consists to approx. 25% of amylose starch and approx. 75% of amylopectin starch.

The molecular structure of the starch, which is largely determined by the degree of branching, the amylose/amylopectin ratio, the average length and distribution of the side chains and the presence of phosphate groups is of prime importance for important functional properties of the starch, resp., its aqueous solutions. Important functional properties which must be mentioned are, for example, solubility, retrogradation behavior, film-forming properties, viscosity, color stability, the gelatination properties and the binding and adhesion properties. Also, starch granule size may be of importance for various applications. The production of high-amylose starches is also of particular interest for certain applications. Furthermore, a modified starch contained in plant cells may advantageously alter the behavior of the plant cells under certain conditions. For example, a reduced starch degradation during the storage of starch-containing organs such as, for example, seeds or tubers, before their processing, for example for starch extraction, is feasible. It is also of interest to produce modified starches which make plant cells or plant organs which contain this starch better suited for processing, for example in the preparation of foodstuffs such as popcorn or cornflakes from corn or of potato chips, potato crisps or potato powder from potatoes. Of particular interest is the improvement of the starches regarding a reduced cold sweetening, i.e. a reduced liberation of reducing sugars (in particular glucose) upon prolonged storage at low temperatures. Potatoes especially are frequently stored at temperatures from 4 to 8° C. to minimize starch degradation during storage. The reducing sugars liberated during this process, in particular glucose, result in undesired browning reactions in the production of potato chips or potato crisps (so-called Maillard reactions).

The starch which can be isolated from plants is frequently adapted to particular industrial purposes with the aid of chemical modifications which, as a rule, require time and money. It seems therefore desirable to find possibilities of generating plants which synthesize a starch whose properties already meet the specific demands of the processing industry and thus combine economical and ecological advantages.

A possibility of providing such plants is, in addition to breeding measures, the direct genetic alteration of the starch metabolism of starch-producing plants by genetic engineering methods. However, a prerequisite therefor is the identification and characterization of the enzymes which participate in starch synthesis modification and starch degradation (starch metabolism) and isolation of the corresponding DNA sequences which encode these enzymes.

The biochemical pathways which lead to the synthesis of starch are essentially known. In plant cells, starch synthesis takes place in the plastids. In photosynthetically active tissues, these plastids are the chloroplasts, in photosynthetically inactive, starch-storing tissues the amyloplasts.

Important enzymes which participate in starch synthesis are, for example, the branching enzymes, ADP glucose pyrophosphorylases, granule-bound starch synthases, soluble starch synthases, debranching enzymes, disproportioning enzymes, plastidic starch phosphorlyases and the R1 enzymes (R1 proteins).

OBJECTS AND SUMMARY OF THE INVENTION

It is an object of the present invention to provide other, or alternative, genetic engineering methods for modifying the starch metabolism in starch-synthesizing plants (for example rye, barley, oats, corn, wheat, sorghum and millet, sago, rice, peas, marrowfat peas, cassava, potatoes, tomatoes, oilseed rape/canola, soybeans, hemp, flax, sunflowers, cowpeas, mung beans, beans, bananas or arrowroot) or suitable nucleic acid molecules by means of which plant cells can be transformed to allow the synthesis of altered advantageous starch varieties.

Such altered starch varieties exhibit, for example, modifications regarding their degree of branching, the amylose/amylopectin ratio, the phosphate content, the starch granule size and/or the average length and distribution of the side chains (i.e. the side chain structure).

It is a further object of the invention to provide methods which allow the generation of transgenic plants which synthesize an altered (modified) starch variety.

Surprisingly, transgenic plant cells or plants which have been transformed with the nucleic acid molecules according to the invention synthesize a starch which is altered in the particular manner according to the invention with regard to its physicochemical properties and/or its side chain structure. In contrast, known starches which were synthesized by transgenic plants do not exhibit alterations according to the invention.

These objects are achieved according to the invention by providing the use forms specified in the claims.

DETAILED DESCRIPTION

The invention therefore relates to a recombinant nucleic acid molecule (nucleotide sequence) comprising a) at least one nucleotide sequence (polynucleotide, resp., nucleic acid molecule) encoding a protein having the function of a soluble starch synthase III or fragments of said nucleotide sequence and b) one or more nucleotide sequences which encode a protein selected from the group A, consisting of proteins having the function of branching enzymes, ADP glucose pyrophosphorylases, granule-bound starch synthases, soluble starch synthases I, II, or other, debranching enzymes, disproportioning enzymes, plastidic starch phosphorylases, R1 enzymes, amylases, and glucosidases, or fragments thereof—preferably, soluble starch synthases I, soluble starch synthases II and/or branching enzymes or fragments thereof—and nucleic acid molecules which hybridize with one of the said nucleotide sequences or fragments thereof, preferably a deoxyribonucleic acid molecule or ribonucleic acid molecule, especially preferably a cDNA molecule. Especially preferred is a nucleic acid molecule which hybridizes specifically with one of said nucleotide sequences or fragments thereof.

Nucleotide sequences which are suitably employed according to the invention and which encode a protein having the function of soluble starch synthase III are disclosed, for example, in EP-A-0779363 and Abel et al., 1996, Plant J. 10(6:981-991 (SEO ID NO:1). The term "nucleotide sequence encoding a protein having the function of a soluble starch synthase III" is to be understood as meaning for the purposes of the present invention in particular those sequences whose encoding region has a length of 3000-4500 bp, preferably 3200-4250 bp, especially preferably 3400-4000 bp and whose homology to the entire encoding region of a nucleic acid encoding a protein which has the function of a starch synthase (SEO ID NO:1) amounts to at least 70%, preferable at least 80%, especially preferably at least 90% and very especially preferably at least 95%.

Nucleotide sequences which are suitable according to the invention and which encode a protein from the group A are, for example, soluble starch synthases (Type I, II or other) or granule-bound starch synthase isoforms (e.g., Hergersberg, 1988, PhD thesis, University of Cologne; Abel, 1995, PhD thesis, FU Berlin; Abel et al., 1996, Plant Journal 10(6): 981-991; Visser et al., 1989, Plant Sci. 64:185-192; van der Leij et al., 1991, Mol. Gen. Genet. 228:240-248; EP-A-0779363; WO 92/11376; WO 96/15248, wherein SSSB has the meaning of soluble starch synthase I, and GBSSII has the meaning of soluble starch synthase II; WO 97/26362; WO 97/44472; WO 97/45545; Delrue et al., 1992, J. Bacteriol. 174: 3612-3620; Baba et al., 1993, Plant Physiol. 103:565-573; Dry et al., 1992, The Plant Journal 2,2: 193-202 or else in the EMBL database entries X74160; X58453; X88789); branching enzyme isoforms (branching enzymes I, IIa, IIb), debranching enzyme isoforms (debranching enzymes, isoamylases, pullulanases) or disproportioning enzyme isoforms, described, for example, in WO 92/14827; WO 95/07335; WO 95/09922; WO 96/19581; WO 97/22703; WO 97/32985; WO 97/42328; Takaha et al., 1993, J. Biol. Chem. 268: 1391-1396 or else in the EMBL database entry X83969, and those for ADP glucose pyrophosphorylases, plastidic starch phosphorylase isoforms and R1 enzymes (R1 proteins), described, for example, in EP-A-0368506; EP-A-0455316; WO 94/28146; DE 19653176.4; WO 97/11188; Brisson et al., 1989, The Plant Cell 1:559-566; Buchner et al., 1996, Planta 199:64-73; Camirand et al., 1989, Plant Physiol. 89(4 Suppl.) 61; Bhatt & Knowler, J. Exp. Botany 41 (Suppl.) 5-7; Lin et al., 1991, Plant Physiol. 95:1250-1253; Sonnewald et al.,1995, Plant Mol. Biol. 27:567-576; DDBJ No. D23280; Lorberth et al., 1998, Nature Biotechnology 16:473-477, and amylases and glucosidases.

The nucleotide sequences which are suitably employed in accordance with the invention are of prokaryotic or eukaryotic origin, preferably of bacterial, fungal or plant origin.

The term "fragment" denotes, for the purposes of the present invention, portions of the nucleic acid molecule according to the invention or of a nucleic acid molecule to be suitably employed in accordance with the invention which has a length of at least 15 bp, preferably at least 150 bp, especially preferably at least 500 bp, but which generally do not exceed a length of 5000 bp, preferably 2500 bp. In particular, the term "fragment" encompasses biologically active molecules.

The term "hybridization" denotes, for the purposes of the present invention, a hybridization under conventional hybridization conditions, preferably under stringent conditions as they are described, for example, by Sambrook et al., Molecular Cloning, A Laboratory Manual, 2nd Edition (1989) Cold Spring Harbor Laboratory Press, Cold Spring Harbor, N.Y.).

Especially preferably, a "specific hybridization" takes place under the following highly stringent conditions:

Hybridization buffer: 2× SSC; 10× Denhardt solution (Ficoll 400+PEG+BSA; ratio 1:1:1); 0.1% SDS; 5 mM EDTA; 50 mM $Na_2HPO_4$; 250 µg/ml herring sperm DNA; 50 µg/ml tRNA; or 0.25 M sodium phosphate buffer pH 7.2; 1 mM EDTA; 7% SDS at a

| | |
|---|---|
| Hybridization temperature of | T = 55 to 68° C., |
| Wash buffer: | 0.2 × SSC; 0.1% SDS and |
| Wash temperature: | T = 40 to 68° C. |

The molecules which hybridize with the nucleic acid molecules according to the invention or with the nucleic acid molecules to be suitably employed in accordance with the invention also encompass fragments, derivatives and allelic variants of the nucleic acid molecules according to the invention or to be suitably employed in accordance with the invention. "Fragments" are not only to be understood as portions of the nucleic acid molecules which are long enough to encode a functionally active portion of the proteins described. The term "derivative" means, within the context of the present invention, that the sequences of these molecules differ from the sequences of the nucleic acid molecules according to the invention or to be suitably employed in accordance with the invention in one or more positions and exhibit a high degree of homology to these sequences. Homology means a sequential identity of at least 60%, preferably over 70%, and especially preferably over 85%, in particular over 90% and very especially preferably over 95%. The deviations relative to the nucleic acid molecules according to the invention or to the nucleic acid molecules to be suitably employed in accordance with the invention may have originated by means of one or more deletions, substitutions, insertions (addition) or recombinations.

Furthermore, homology means that a functional and/or structural equivalence exists between the nucleic acid molecules in question and the proteins encoded by them. The nucleic acid molecules Which are homologous to the molecules according to the invention or to the molecules to be suitably employed in accordance with the invention and which constitute derivatives of these molecules are, as a rule, variations of these molecules which constitute modifications which exert the same, a virtually identical or a similar biological function. They may be naturally occurring variations, for example sequences from other plant species or mutations, it being possible for these mutations to have occurred naturally or to have been introduced by natural mutagenesis. The variations may further be synthetic sequences. The allelic variants may be naturally occurring variants or else synthetic variants or variants generated by recombinant DNA technology.

The nucleic acid molecules according to the invention or to be suitably employed in accordance with the invention may be DNA molecules, in particular cDNA molecules, or, if appropriate, the combination of genomic molecules. The nucleic acid molecules according to the invention or to be suitably employed in accordance with the invention may furthermore be RNA molecules. The nucleic acid molecules according to the invention or to be suitably employed in accordance with the invention or fragments thereof may have been obtained, for example, from natural sources, generated by means of recombinant technology or generated by synthesis.

To express the nucleic acid molecules according to the invention or the nucleic acid molecules to be suitably employed in accordance with the invention in sense or antisense orientation in plant cells, they are linked with the regulatory DNA elements which ensure transcription in plant cells. These include in general, promoters. In general, any promoter which is active in plant cell is suitable for expression. The promoter may have been chosen to in such a way that expression is constitutive or only in a particular tissue, at a particular point in time of plant development or at a point in time determined by external factors which can be, for example, chemically or biologically inducible. Relative to the transformed plant, the promoter can be homologous or heterologous, as can be the nucleotide sequence. Examples of suitable promoters are the cauliflower mosaic virus 35S RNA promoter and the ubiqutin-promotor derived from corn for constitutive expression, the palatin promoter B33 (Rocha-Sosa et al., 1989, EMBO J., 8:23-29) for tuber-specific expression in potatoes or a promoter which ensures expression only in photosynthetically active tissues, for example the ST-LS1 promoter (Stockhaus et al., 1987, Proc. Natl. Acad. Sci. USA 84: 7943-7947; Stockhaus et al., 1989, EMBO J. 8: 2445-2451) or, the Ca/b-promotor (e.g., U.S. Pat. No. 5,656,496; U.S. Pat. No. 5,639,952; Barisal et al., Proc. Nati. Acad. Sci. USA 89, (1992), 3654-3658) and the rubisco SSU-Promotor (e.g., U.S. Pat. No. 5,034,322; U.S. Pat. No. 4,962,028) or for a endosperm-specific expression the glutelin promotor (Leisy et al., Plant Mol. Biol. 14, (1990), 41-50; Zheng et al., Plant J. 4, (1993), 357-366; Yoshihara et al., FEBS Left. 383, (1996), 213-218), the shrunken-1 promoter (Werr et al., EMBO J. 4, (1985), 1373-1380), the wheat HMG 10 promoter, the USP promotor, the phaseolin promotor or promoters from maize zein genes (Pedersen et al., Cell 29, (1982), 1015-1026; Quatroccio et al., Plant Mol. Biol. 15 (1990), 81-93).

A termination sequence which terminates the nucleic acid molecule according to the invention may serve to correctly end transcription and to add to the transcript a poly-A tail, which is considered to have a function in stabilizing the transcripts. Such elements have been described in the literature (cf. Gielen et al., 1989, EMBO J. 8:23-29) and are, as a rule, exchangeable as desired.

The nucleic acid molecules according to the invention or to be suitably employed in accordance with the invention can be used for generating transgenic plant cells and plants which show an increase and/or reduction in the activity of the soluble starch synthase III and of at least one further enzyme of starch metabolism. To this end, the nucleic acid molecules according to the invention or to be suitably employed in accordance with the invention are introduced into suitable vectors, provided with the regulatory nucleic acid sequences which are necessary for efficient transcription in plant cells, and introduced into plant cells. On the one hand, there is the possibility of using the nucleic acid molecules according to the invention or the nucleic acid molecules to be suitably employed in accordance with the invention for inhibiting the synthesis of the endogenous soluble starch synthase III and/or of at least one further protein from the group A in the cells. This may be achieved with the aid of antisense constructs, in-vivo mutagenesis, a cosuppression effect which occurs, or with the aid of suitably constructed ribozymes. On the other hand, the nucleic acid molecules according to the invention or to be suitably employed in accordance with the invention can be used for expressing the soluble starch synthase III and/or at least one further protein from the group A in cells of transgenic plants and thus lead to an increased activity, in the cells, of the enzymes which have been expressed in each case.

In addition, there exists the possibility of using the nucleic acid molecules according to the invention or to be suitably employed in accordance with the invention for inhibiting the synthesis of the endogenous soluble starch synthase III and the overexpression of at least one further protein from the group A in the cells. Finally, the nucleic acid molecules according to the invention or to be suitably employed in accordance with the invention may also be used for expressing the soluble starch synthase III and for inhibiting at least one further protein from the group A in cells of transgenic plants. The two last-mentioned embodiments of the invention thus lead, in the cells, to a simultaneous inhibition and increase in activity of the enzymes which are inhibited or expressed, respectively.

The invention furthermore relates to a vector comprising a nucleic acid molecule according to the invention.

The term "vector" encompasses plasmids, cosmids, viruses, bacteriophages and other vectors conventionally used in genetic engineering which contain the nucleic acid molecules according to the invention and which are suitable for transforming cells. Such vectors are preferably suitable for transforming plant cells. Especially preferably, they permit integration of the nucleic acid molecules according to the invention, if appropriate together with flanking regulatory regions, into the genome of the plant cell. Examples are binary vectors such as pBinAR or pBinB33, which can be employed in *agrobacteria*-mediated gene transfer.

In a preferred embodiment, the vector according to the invention is distinguished by the fact that the nucleotide sequence encoding a protein having the function of of a soluble starch synthase III or fragments thereof is present in sense or in antisense orientation.

In a further preferred embodiment, the vector according to the invention is distinguished by the fact that the nucleotide sequence which encodes one or more proteins selected from the group A or fragments thereof is present in sense or in antisense orientation.

In yet a further preferred embodiment, the vector according to the invention is distinguished by the fact that the nucleotide sequence which encodes a plurality of proteins selected from the group A or fragments thereof is present partly in sense and partly in antisense orientation.

Very especially preferably, the vector according to the invention comprises one or more regulatory elements which ensure transcription or synthesis of an RNA in a prokaryotic or eukaryotic cell.

In addition, it is possible to introduce, by means of customary techniques of molecular biology (see, for example, Sambrook et al., 1989, Molecular Cloning, A Laboratory Manual, 2nd Edition, Cold Spring Harbor Laboratory Press, Cold Spring Harbour, N.Y.), various mutations into the DNA sequences according to the invention or the DNA molecules to be suitably employed in accordance with the invention, which leads to the synthesis of proteins with biological properties which may be altered. On the one hand, it is possible to generate deletion mutants in which sequences are generated, by progressive deletions from the 5' or from the 3' end of the encoding DNA sequences which lead to the synthesis of analogously truncated proteins. For example, such deletions at the 5' end of the DNA sequence allow the targeted production of enzymes which, due to the removal of the relevant transit or signal sequences, are no longer localized in their original (homologous) compartment, but in the cytosol, or which, due to the addition of other signal sequences, are localized in one or more other (heterologous) compartments (for example plastid, vacuole, mitochondrion, apoplast).

On the other hand, it is also feasible to introduce point mutations in positions where an altered amino acid sequence affects, for example, the enzyme activity or the regulation of the enzyme. Thus, it is possible to generate, for example mutants which have an altered $K_M$ or $k_{cat}$ value or which are no longer subject to the regulatory mechanisms normally present in the cell, e.g., via allosteric regulation or covalent modification.

For the genetic engineering manipulation in prokaryotic cells, the DNA sequences according to the invention or to be suitably employed in accordance with the invention or fragments of these sequences can be introduced into plasmids which permit mutagenesis or an altered sequence by the recombination of DNA sequences. Base exchanges may be performed or natural or synthetic sequences may be added, with the aid of standard methods in molecular biology (cf. Sambrook et al., 1989, loc.cit.). To link the DNA portions to each other, adaptors or linkers may be attached to the portions. Furthermore, manipulations which provide suitable restriction cleavage sites or which remove excessive DNA or restriction cleavage sites which are no longer needed may be employed. Where insertions, deletions or substitutions are suitable, in-vitro mutagenesis, primer repair, restriction or ligation may be employed. The analytical methods which are generally carried out are sequence analysis, restriction analysis and, if appropriate, other methods of biochemistry and molecular biology.

The invention furthermore relates to a transgenic host cell exhibiting an altered starch metabolism, in particular to prokaryotic or eukaryotic cells, preferably bacterial or plant (monocotyledonous or dicotyledenous) cells (for example of *E.coli*, Agrobacterium, Solananceae, Poideae, rye, barley, oats, corn, wheat, sorghum and millet, sago, rice, peas, marrowfat peas, cassava, potatoes, tomatoes, oilseed rape/canola, soybeans, hemp, flax, sunflowers, cowpeas, mung beans, beans, bananas or arrowroot) which contain one or more nucleic acid molecules according to the invention or one or more vectors according to the invention, or which is derived from such a cell.

Yet another subject of the invention is a transgenic host cell exhibiting an altered starch metabolism, in particular prokaryotic or eukaryotic cells, preferably bacterial or plant cells (for example of E.coli, Agrobacterium, Solananceae, Poideae, rye, barley, oats, corn, wheat, sorghum and millet, sago, rice, peas, marrowfat peas, cassava, potatoes, tomatoes, oilseed rape/canola, soybeans, hemp, flax, sunflowers, cowpeas, mung beans, beans, bananas or arrowroot) comprising a) at least one nucleotide sequence encoding a protein having the function of a soluble starch synthase III or fragments thereof, and b) one or more nucleotide sequences encoding a protein selected from the group A or fragments thereof or nucleotide sequences which hybridize with the said nucleic acid molecules or which is derived from such a cell.

Host cells according to the invention cannot only be generated by using the nucleic acid molecules according to the invention, but also by means of successive transformation (e.g., by so-called supertransformation), by employing a plurality of portions of the nucleotide sequence according to the invention or a plurality of vectors comprising portions of the nucleotide sequence according to the invention which encode a protein having the function of a soluble starch synthase III and additionally encode one or more proteins selected from the group A consisting of branching enzymes, ADP glucose pyrophosphorylases, granule-bound starch synthases, soluble starch synthases I, II or other, debranching enzymes, disproportioning enzymes, plastidic starch phosphorylases, R1 enzymes, fragments thereof, and nucleic acid molecules which hybridize with one of said nucleotide sequences or fragments thereof, in a plurality of cell transformation steps. Hereby, the cell is subsequently or simultaneously transformed in any order with a) at least one nucleic acid molecule encoding a protein having the function of a soluble starch synthase III, a fragment thereof or a vector comprising said nucleic acid molecule and b) one or more nucleic acid molecules encoding a protein selected from the group A consisting of branching enzymes, ADP glucose pyrophosphorylases, granule-bound starch synthases, soluble starch synthases I, II or other, debranching enzymes, disproportioning enzymes, plastidic starch phosphorylases, R1 enzymes; or fragments thereof, —preferably soluble starch syntheses I, soluble starch syntheses II and/or branching enzymes or fragments thereof—, and nucleic acid molecules which hybridize with one of said nucleotide sequences or one or more vectors comprising one or more of the said nucleic acid molecules.

Another object of the invention is a method of generating a transgenic host cell, bacterial cell, plant cell or plant which synthesizes a modified starch, which comprises integrating into the genome of a cell a) at least one nucleic acid molecule encoding a protein having the function of a soluble starch synthase III, a fragment thereof or a vector comprising said nucleic acid molecule and b) one or more nucleic acid molecules encoding a protein selected from the group A consisting of branching enzymes, ADP glucose pyrophosphorylases, granule-bound starch synthases, soluble starch synthases I, II or other, debranching enzymes, disproportioning enzymes, plastidic starch phosphorylases, and R1 enzymes, or fragments thereof, —preferably, soluble starch synthases I, soluble starch synthases II and/or branching enzymes or fragments thereof—, and nucleic acid molecules which hybridize with one of said nucleotide sequences or one or more vectors comprising one or more of the said nucleic acid molecules.

A further embodiment of the present invention relates to a method of generating a transgenic host cell, bacterial cell, plant cell or plant which synthesizes a modified starch, which comprises integrating one or more nucleic acid molecules according to the invention or one or more vectors according to the invention into the genome of a cell.

Providing the nucleic acid molecules according to the invention makes it possible to engage in the starch metabolism of plants, with the aid of genetic engineering methods, and to alter it in such a way that the result is the synthesis of a modified starch which is altered relative to starch synthesized in wild-type plants with regard to, for example, structure, water content, protein content, lipid content, fiber content, ash/phosphate content, amylose/amylopectin ratio, molecular mass distribution, degree of branching, granule size, granule shape and crystallization, or else in its physicochemical properties such as flowing and absorption behavior, gelatinization temperature, viscosity, thickening capacity, solubility, gel structure, transparency, thermal stability, shear stability, stability to acids, tendency to undergo retrogradation, gelling, freeze-thaw-stability, complex formation, iodine binding, film formation, adhesion power, enzyme stability, digestibility or reactivity.

There is also the possibility of increasing the yield in suitably genetically engineered plants by increasing the activity of proteins which are involved in the starch metabolism, for example by overexpressing suitable nucleic acid molecules, or by providing mutants which are no longer subject to the cell's regulatory mechanisms and/or which exhibit different temperature dependencies relating to their activity. A particularly pronounced increase in yield may be the result of increasing the activity of one or more proteins which are involved in the starch metabolism in specific cells of the starch-storing tissues of transformed plants such as, for example, in the tuber in the case of potatoes or in the endosperm of corn or wheat. The economic importance and the advantages of these possibilities of engaging in the starch metabolism are enormous.

When expressing the nucleic acid molecules according to the invention or to be suitably employed in accordance with the invention in plants, it is possible, in principle, for the synthesized protein to be localized in any desired compartment of the plant cell. To achieve location in a particular compartment (cytosol, vacuole, apoplast, plastids, mitochondria), the transit or signal sequence which ensures location must, if necessary, be deleted (removed) and the remaining encoding region must, if necessary, be linked to DNA sequences which ensure location in the particular compartment. Such sequences are known (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). To ensure the location in a particular plant part or tissue specific promoters may be used which are well known to the person skilled in the art.

The generation of plant cells with a reduced activity of a protein involved in the starch metabolism can be achieved, for example, by expressing a suitable antisense RNA, a sense RNA for achieving a cosuppression effect, in-vivo mutagenesis or by expressing a suitably constructed ribozyme which specifically cleaves transcripts which encode one of the proteins involved in the starch metabolism, using a nucleic acid molecule according to the invention, preferably by expressing an antisense transcript.

To this end, it is possible to use, on the one hand, a DNA molecule which encompasses all of the sequence which encodes a protein involved in the starch metabolism inclusive of any flanking sequences which may be present, as well as DNA molecules which only encompass fragments of the encoding sequence, these fragments having a minimum length of 15 bp, preferably of at least 100-500 bp, in particular over 500 bp. As a rule, DNA molecules are used which are shorter than 5000 bp, preferably shorter than 2500 bp.

It is also possible to use DNA sequences which exhibit a high degree of homology to the sequences of the DNA molecules according to the invention, but are not fully identical with them. The minimum homology should exceed approx. 65%. The use of sequences with a homology of approximately 75 to 85% and, in particular, approximately 85 to 95%, is preferred.

The expression of ribozymes for reducing the activity of specific proteins in cells is known to those skilled in the art and described, for example, in EP-B1-0 321 201. The expression of ribozymes in plant cells was described, for example, by Feyter et al. (Mol. Gen. Genet. 250 (1996), 329-338).

Further, the proteins involved in the starch metabolism may also be reduced in the plant cells according to the invention by so-called "in-vivo mutagenesis", where a hybrid RNA-DNA-oligonucleotide ("chimeroplast") is introduced into cells by means of transforming them (Kipp P. B. et al., Poster Session at the "5$^{th}$ International Congress of Plant Molecular Biology, 21-27, September 1997, Singapore; R. A. Dixon and C. J. Arntzen, Meeting report on "Metabolic Engineering in Transgenic Plants", Keystone Symposia, Copper Mountain, Colo., USA, TIBTECH 15 (1997), 441-447; International Patent Application WO 95/15972; Kren et al., Hepatology 25 (1997), 1462-1468; Cole-Strauss et al., Science 273 (1996),1386-1389).

A fragment of the DNA component of the RNA-DNA-oligonucleotide used for this purpose is homologous to a nucleic acid sequence of an endogenous protein, but exhibits a mutation in comparison with the nucleic acid sequence of the endogenous protein or comprises a heterologous region enclosed by the homologous regions.

Base pairing of the homologous regions of the RNA-DNA-oligonucleotide and of the endogenous nucleic acid molecule followed by homologous recombination allows the mutation or heterologous region comprised in the DNA component of the RNA-DNA-oligonucleotide to be transferred into the genome of a plant cell. This leads to a reduced activity of the protein involved in the starch metabolism.

Alternatively, the enzyme activities which are involved, in the plant cells, in the starch metabolism may be reduced by a cosuppression effect. This method is described, for example, by Jorgensen (Trends Biotechnol. 8 (1990), 340-344), Niebel et al., (Curr. Top. Microbiol. Immunol. 197 (1995), 91-103), Flavell et al. (Curr. Top. Microbiol. Immunol. 197 (1995), 43-46), Palaqui and Vaucheret (Plant. Mol. Biol. 29 (1995), 149-159), Vaucheret et al., (Mol. Gen. Genet. 248 (1995), 311-317), de Borne et al. (Mol. Gen. Genet. 243 (1994), 613-621).

To inhibit the synthesis, in the transformed plants, of a plurality of enzymes involved in starch biosynthesis, it is possible to use DNA molecules for transformation which simultaneously comprise, in antisense orientation and under the control of a suitable promoter, a plurality of regions which encode the relevant enzymes. Each sequence may be under the control of its promoter, or, alternatively, the sequences can be transcribed by a joint promoter as a fusion, so that the synthesis of the proteins in question is inhibited to approximately the same or to a different extent. As regards the length of the individual encoding regions which are used in such a construct, what has already been said above for the generation of antisense constructs also applies here. In principle, there is no upper limit for the number of antisense fragments transcribed starting from a promoter in such a DNA molecule. However, the resulting transcript should not, as a rule, exceed a length of 25 kb, preferably 15 kb.

Therefore, the nucleic acid molecules according to the invention or to be suitably employed in accordance with the invention make it possible to transform plant cells and simultaneously to inhibit the synthesis of a plurality of enzymes.

Moreover, it is possible to introduce the nucleic acid molecules according to the invention or to be suitably employed in accordance with the invention into traditional mutants which are deficient or defective, with regard to one or more starch biosynthesis genes (Shannon and Garwood, 1984, in Whistler, BeMiller and Paschall, Starch: Chemistry and Technology, Academic Press, London, 2nd Edition: 25-86). These defects can relate, for example, to the following proteins: granule-bound starch synthase (GBSS I) and soluble starch synthases (SS I, II, III or other), branching enzymes (BE I, IIa and IIb), debranching enzymes (R-enzymes, isoamylases, pullulanases), disproportioning enzymes and plastidic starch phosphorylases.

The present invention thus also relates to transgenic plant cells obtainable by a process according to the invention which have been transformed with a vector or nucleic acid molecule according to the invention or the nucleic acid molecules to be suitably employed in accordance with the invention, and to transgenic plant cells or plants derived from such transformed cells. The cells according to the invention contain one or more nucleic acid molecules according to the invention or to be suitably employed in accordance with the invention, this preferably being linked to one or more regulatory DNA elements (for example promoter, enhancer, terminator) which ensure the transcription in plant cells, in particular a promoter. The cells according to the invention can be distinguished from naturally occurring plant cells, inter alia, by the fact that they contain a nucleic acid molecule according to the invention which does not occur naturally in these cells, or by the fact that such a molecule exists integrated at a location in the cell's genome where it does not occur otherwise, i.e. in a different genomic environment. Furthermore, the transgenic plant cells according to the invention can be distinguished from naturally occurring plant cells by the fact that they contain at least one copy of a nucleic acid molecule according to the invention stably integrated into their genome, if appropriate in addition to copies of such a molecule which occur naturally in the cells, resp., the nucleic acid molecules to be suitably employed in accordance with the invention. If the nucleic acid molecule(s) introduced into the cells is (are) additional copies to molecules which already occur naturally in the cells, then the plant cells according to the invention can be distinguished from naturally occurring plant cells in particular by the fact that this additional copy, or these additional copies, is, or are, localized at sites in the genome at which it does not occur naturally, or they do not occur naturally. This can be checked, for example, with the aid of a Southern blot analysis.

Preferred plant cells according to the invention are those in which the enzyme activity of individual enzymes which are involved in the starch metabolism is increased and/or reduced by in each case at least 10%, especially preferably at least 30% and very especially preferably by at least 50%.

Moreover, the plant cells according to the invention can be distinguished from naturally occurring plant cells preferably by at least one of the following features: if the nucleic acid molecule which has been introduced is heterologous relative to the plant cell, the transgenic plant cells exhibit transcripts of the nucleic acid molecules which have been introduced. These can be detected by, for example, northern blot analysis. For example, the plant cells according to the invention contain one or more proteins encoded by a nucleic acid molecule according to the invention, resp., the nucleic acid molecules to be suitably employed in accordance with the invention, which has been introduced. This can be detected by, for example, immunological methods, in particular by a western blot analysis.

If the nucleic acid molecule according to the invention, resp., the nucleic acid molecules to be suitably employed in accordance with the invention which has been introduced is homologous relative to the plant cell, the cells according to the invention can be distinguished from naturally occurring cells, for example, on the basis of the additional expression of nucleic acid molecules according to the invention, resp., the nucleic acid molecules to be suitably employed in accordance with the invention. For example, the transgenic plant cells contain more or fewer transcripts of the nucleic acid molecules according to the invention, resp., the nucleic acid molecules to be suitably employed in accordance with the invention. This can be detected by, for example, northern blot analysis. "More" or "fewer" in this context means preferably at least 10% more or fewer, preferably at least 20% more or fewer and especially preferably at least 50% more or fewer transcripts than corresponding untransformed cells. Furthermore, the cells preferably exhibit a corresponding increase or decrease in the content of the proteins encoded by the introduced nucleic acid molecules (at least 10%, 20% or 50%).

The transgenic plant cells can be regenerated to entire plants by techniques known to those skilled in the art. The plants obtainable by regenerating the transgenic plant cells according to the invention, and processes for the generation of transgenic plants by regenerating entire plants from the plant cells according to the invention, are also subject matter of the present invention. Another subject of the invention are plants which comprise the transgenic plant cells according to the invention. In principle, the transgenic plants can be plants of any species, i.e. not only monocotyledonous, but also dicotyledonous plants. The plants are preferably crop plants and starch-storing plants such as, for example, cereal species (rye, barley, oats, corn, wheat, sorghum and millet, etc.), sago, rice, peas, marrowfat peas, cassava, potatoes, tomatoes, oilseed rape/canola, soybeans, hemp, flax, sunflowers, cowpeas, mung beans or arrowroot.

The invention also relates to propagation material of the plants according to the invention, for example fruits, seeds, tubers, root stocks, seedlings, cuttings, calli, protoplasts, cell cultures and the like.

Altering the enzymatic activities of the enzymes involved in the starch metabolism results in the synthesis, in the plants generated by the process according to the invention, of a starch with an altered structure.

A large number of cloning vectors is available for preparing the introduction of foreign genes into higher plants, vectors which comprise a replication signal for *E. coli* and a marker gene for the selection of transformed bacterial cells. Examples of such vectors are pBR322, pUC series, M13mp series, pACYC184 and the like. The desired sequences can be introduced into the vector at a suitable restriction cleavage site. The plasmid obtained is used for transforming *E. coli* cells. Transformed *E. coli* cells are grown in a suitable medium, and then harvested and lysed. The plasmid is recovered. The analytical methods for characterizing the plasmid DNA obtained are generally restriction analyses, gel electrophoreses and other methods of biochemistry and molecular biology (Sambrook et al. loc.cit.). After each manipulation, the plasmid DNA can be cleaved and DNA fragments obtained linked with other DNA sequences. Each plasmid DNA sequence can be cloned into the same or other plasmids.

A large number of techniques is available for introducing DNA into a plant host cell. These techniques encompass the transformation of plant cells with T-DNA using *Agrobacterium tumefaciens* or *Agrobacterium rhizogenes* as transformants, protoplast fusion by means of polyethylene glycol (PEG), injection, DNA electroporation, the introduction of DNA by means of the biolistic method, and other possibilities (Gene Transfer to Plants. pp. 24-29, eds.: Potrykus, I. and Spangenberg, G., Springer Verlag Berlin Heidelberg 1995).

The injection and electroporation of DNA into plant cells require no particular aspects of the plasmids or the DNA used. Simple plasmids such as, for example, pUC derivatives can be used. However, if entire plants are to be regenerated from such transformed cells, the presence of a selectable marker gene is required.

Depending on the method of introducing desired genes into the plant cell, further DNA sequences may be required. If, for example, the Ti or Ri plasmid is used for transforming the plant cell, at least the right border, but frequently the right and left border of the Ti and Ri plasmid T-DNA must be linked to the genes to be introduced as a flanking region.

If *agrobacteria* are used for the transformation, the DNA to be introduced must be cloned into specific plasmids, either into an intermediate vector or into a binary vector. The intermediate vectors can be integrated into the *agrobacterial* Ti or Ri plasmid by homologous recombination owing to sequences which are homologous to sequences in the T-DNA. The former also contains the vir region, which is required for the T-DNA transfer. Intermediate vectors calmot replicate in *agrobacteria*. The intermediate vector can be transferred to *Agrobactedum* tumefaciens by means of a helper plasmid (conjugation). Binary vectors are capable of replication in *E.coli* and in *agrobacteria*. They contain a selection marker gene and a linker orpolylinker which are framed by the left and right T-DNA border region. They can be transformed directly into the *agrobacteria* (Holsters et al. (1978) Mol. Gen. Genet. 163:181-187). The agrobacterium which acts as the host cell should contain a plasmid carrying a vir region. The vir region is required for transferring the T-DNA into the plant cell. Additional T-DNA may be present. The agrobacterium thus transformed is used for transforming plant cells.

The use of T-DNA for transforming plant cells has been researched intensively and been described in EP 120516; Hoekema, In: The Binary Plant Vector System Offsetdrukkerij Kanters B. V., Alblasserdam (1985), Chapter V; Fraley et al., Crit. Rev. Plant. Sci., 4: 1-46 and An et al. (1985) EMBO J. 4: 277-287.

To transfer the DNA into the plant cell, plant explants can expediently be cocultured with *Agrobacterium tumefaciens* or *Agrobacterium rhizogenes*. Entire plants can then be regenerated from the infected plant material (for example leaf section, stalk sections, roots, but also protoplasts, or plant cells grown in suspension culture) in a suitable medium which can contain, for example, antibiotics or biocides for selecting transformed cells. The resulting plants can then be examined for the presence of the DNA which has been introduced. Other possibilities of introducing foreign DNA using the biolistic method or by protoplast transformation are known (cf., for example, Willmitzer, L, 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge).

While the transformation of dicotyledonous plants via Ti-plasmid vector systems with the aid of *Agrobacterium tumefaciens* is well established, more recent work suggests that even monocotyledonous plants are indeed accessible to transformation by means of agrobacterium-based vectors (Chan et al., Plant Mol. Biol. 22 (1993), 491-506; Hiei et al., Plant J. 6 (1994), 271-282).

Alternative systems for the transformation of monocotyledonous plants are the transformation by means of the biolistic method, protoplast transformation, the electroporation of partially permeabilized cells, and the introduction of DNA by means of glass fibers.

Specifically different methods have been described in the literature for the transformation of corn (cf., for example, WO95/06128, EP 0 513 849; EP 0 465 875). EP 292 435 describes a method with the aid of which fertile plants can be obtained starting from a mucus-free, friable, granular corn callus. In this context, Shillito et al. (Bio/technology 7 (1989), 581) have observed that the capability of regenerating fertile plants requires starting from callus suspension cultures from which a dividing protoplast culture with the capability of regenerating plants can be made. Prioli and Söndahl (Bio/Technology 7 (1989), 589) also describe the regeneration and obtaining of fertile corn plants from corn protoplasts.

Once the introduced DNA is integrated into the genome of the plant cell, it is, as a rule, stable therein and is also retained in the progeny of the originally transformed cell. It normally contains a selection marker which mediates the transformed plant cells resistance to a biocide or an antibiotic such as kanamycin, G 418, bleomycin, hygromycin or phosphinothricin and the like. The individual marker chosen should therefore allow the selection of transformed cells over cells which lack the introduced DNA.

Within the plant, the transformed cells grow in the customary manner (see, also, McCormick et al. (1986) Plant Cell Reports 5:81-84). The resulting plants can be grown normally and hybridized with plants which have the same transformed germplasm or other germplasm. The resulting hybrids have the corresponding phenotypic features.

Two or more generations should be grown to ensure that the phenotypic feature is stably retained and inherited. Also, seeds or the like should be harvested to ensure that the phenotype in question or other features have been retained.

Due to the expression of a nucleic acid molecule according to the invention, the transgenic plant cells and plants according to the invention synthesize a starch whose, for example, physico-chemical properties are altered in comparison with starch synthesized in wild-type plants.

Yet a further subject of the invention is the starch obtainable from a plant cell according to the invention, a plant according to the invention, its propagation material or a process according to the invention.

Yet another subject of the invention is a process for the production of starch in a manner known per se, in which host cells, plant cells, plants, plant parts or propagation material according to the invention is processed, resp., integrated into the process.

In a preferred embodiment, the starch according to the invention is distinguished in that its phosphate content is reduced by at least 30%, preferably at least 50%, especially preferably at least 70% and very especially preferably at least 90% in comparison with a starch obtainable from an untransformed cell or plant (i.e. the wild type) and in that its glucan content (cf. Fraction 3 in Example No. 13) after isoamylase treatment in the exclusion volume of an HPLC column system composed of 2 TSK-gel 2000SW columns connected in series and one TSK-gel 3000SW column in 10 mM sodium acetate, pH 3.0 (at a flow rate of 0.35 ml/min as shown in Example No. 13) is increased by at least 50%, preferably at least 150%, especially preferably at least 300% and very especially preferably at least 500%.

In a further embodiment, the starch according to the invention is distinguished in that its phosphate content is increased by at least 10%, preferably at least 30%, and especially preferably at least 50% in comparison with a starch obtainable from an untransformed cell or plant (i.e. the wild type) and in that its glucan content (cf. Fraction 3 in Example No. 13) after isoamylase treatment in the exclusion volume of an HPLC column system composed of 2 TSK-gel 2000SW columns connected in series and one TSK-gel 3000SW column in 10 mM sodium acetate, pH 3.0 (at a flow rate of 0.35 ml/min as shown in Example No. 13) is increased by at least 50%, preferably at least 150%, especially preferably at least 300% and very especially preferably at least 500%. Processes for extracting the starch from plants or starch-storing plant organs are known to those skilled in the art. Processes for extracting starch from corn kernels are described, for example, by Eckhoff et al. (Cereal Chem. 73 (1996) 54-57). As a rule, the extraction of maize starch on an industrial scale is performed by wet milling. Moreover, processes for extracting the starch from a variety of starch-storing plants are described, for example in "Starch: Chemistry and Technology (Editors: Whistler, BeMiller and Paschall (1994), 2nd Edition, Academic Press Inc. London Ltd; ISBN 0-12-746270-8; see, for example, Chapter XII, pages 412-468; corn and sorghum starches: production; by Watson; Chapter XIII, pages 469-479: tapioca, arrowroot and sago starches: production; by Corbishley and Miller; Chapter XIV, pages 479-490: potato starch: production and uses; by Mitch; Chapter XV, pages 491 to 506: wheat starch: production, modification and uses; by Knight and Oson; and Chapter XVI, pages 507 to 528: rice starch: production and uses; by Rohmer and Klem). Devices normally used in processes for extracting starch from plant material are separators, decanters, hydrocyclones, spray driers and fluidized-bed driers.

A further embodiment of the present invention also includes the use of the starch according to the invention for industrial application, preferably for the production of foodstuffs, packaging materials or disposable products.

The starch according to the invention can be chemically and/or physically modified by processes known to those skilled in the art and is suitable, in its unmodified or modified form, for a variety of applications in the food or non-food sector.

In principle, the possible uses of the starch according to the invention can be divided into two important sectors. One sector encompasses the hydrolysis products of the starch, mainly glucose and glucose units, which are obtained by enzymatic or chemical methods. They are used as starting material for other chemical modifications and processes such as fermentation. What may be important here is the simplicity and inexpensive design of a hydrolysis process as is currently performed essentially enzymatically using amyloglucosidase. What would be feasible is a financial saving by using less enzyme. This could be caused by altering the structure of the starch, for example increasing the surface area of the granule, better degradability by a lower degree of branching, or a sterical structure which limits the accessibility for the enzymes employed.

The other sector in which the starch according to the invention can be used as a so-called native starch, due to its polymeric structure, can be divided into two further fields of application:

1. The Food Industry

Starch is a traditional additive to a large number of foodstuffs in which its function is essentially to bind aqueous additives or to cause an increased viscosity or else increased gelling. Important characteristics are the flowing characteristics, the sorptive characteristics, the swelling temperature, the gelatinization temperature, the viscosity, the thickening power, starch solubility, transparency, gel structure, thermal stability, shear stability, stability to acids, the tendency to undergo retrogradation, the film-forming capacity, the freeze-thaw-stability, digestibility and the ability of forming complexes with, for example, inorganic or organic ions.

2. The Non-Food Industry

In this important sector, starch is employed as auxiliary for various preparation processes or as an additive in products. When using starch as an auxiliary, mention must be made, in particular, of the paper and board industry. Starch acts mainly for retardation purposes (retaining solids), binding filler particles and fine, as a stiffener and for dehydration. Moreover, the advantageous properties of the starch regarding stiffness, hardness, sound, touch, luster, smoothness, bonding strength and the surfaces.

2.1. Paper and Board Industry

Within the papermaking process, four fields of application must be distinguished, i.e. surface, coating, mass and spraying. With 80% of the consumption, the surface starch accounts usually for the greatest starch quantity, 8% are used as coating starch, 7% as mass starch and 5% as spraying starch.

The demands on starch with regard to surface treatment are essentially high whiteness, an adapted viscosity, highly-stable viscosity, good film formation and low dust formation. When used for coating, the solids content, a suitable viscosity, a high binding capacity and a high pigment affinity play an important role. Of importance when used as additive to the mass is rapid, uniform, loss-free distribution, high mechanical strength and complete retention in paper cloth. If the starch is used in the spraying sector, again, an adapted solids content, high viscosity and a high binding capacity are of importance.

2.2. The Adhesives Industry

An important field of application for starches is in the adhesives industry, where the potential uses can be divided into four subsections: the use as a pure starch paste, the use in starch pastes which have been treated with specialty chemicals, the use of starch as additive to synthetic resins and polymer dispersions, and the use of starches as extenders for synthetic adhesives. 90% of the starch-based adhesives are employed in the sectors production of corrugated board, production of paper sacks and bags, production of composite materials for paper and aluminum, production of boxboard and gumming adhesive for envelopes, stamps and the like.

2.3. Textile Industry and Textile Care Products Industry

An important field of application for starches as auxiliaries and additives is the sector production of textiles and textile care products. The following four fields of application must be distinguished within the textile industry: the use of starch as sizing agent, i.e. as auxiliary for smoothing and strengthening the burring behavior as a protection from the tensile forces applied during weaving, and for increasing abrasion resistance during weaving, starch as a textile finishing agent, in particular after quality-reducing pretreatments such as bleaching, dyeing and the like, starch as thickener in the preparation of dye pastes for preventing bleeding, and starch as additive to warping agents for sewing yarns.

2.4. Construction Materials Industry

The fourth field of application is the use of starches as additives in construction materials. An example is the production of gypsum plasterboards, where the starch which is admixed to the gypsum slurry gelatinizes with the water, diffuses to the surface of the plaster core and there binds the board to the core. Other fields of application are the admixture to rendering and mineral fibers. In the case of ready-mixed concrete, starch products are employed for delaying binding.

2.5. Soil Stabilization

A limited market for starch products is the production of soil stabilizers, which are employed for the temporary protection of the soil particles from water when the soil is disturbed artificially. According to present knowledge, product combinations of starch and polymer emulsions equal the previously employed products with regard to their erosion- and crust-reducing effect, but are markedly less expensive.

2.6. Use in Crop Protection Products and Fertilizers

One field of application for using starch is in crop protection products for altering the specific properties of the products. Thus, starches are employed for improving the wettability of crop protection products and fertilizers, for the metered release of the active ingredients, for converting liquid active ingredients, volatile active ingredients and/or active ingredients with an offensive odor into microcrystalline, stable, shapable substances, for mixing incompatible compounds and for extending the duration of action by reducing decomposition.

2.7. Pharmaceuticals, Medicine and the Cosmetics Industry

Another field of application is the sector of the pharmaceuticals, medicine and cosmetics industry. In the pharmaceuticals industry, starches are employed as binders for tablets or for diluting the binder in capsules. Moreover, starches are used as tablet disintegrants, since they absorb fluids after swallowing and swell within a short time to such an extent that the active ingredient is liberated. Medicinal lubricating powders and wound powders are starch-based for reasons of quality. In the cosmetics sector, starches are employed, for example, as carriers of powder additives such as fragrances and salicylic acid. A relatively large field of application for starch is toothpaste.

2.8. Addition of Starch to Coal and Briquettes

A field of application for starch is as an additive to coal and briquettes. With an addition of starch, coal can be agglomerated, or briquetted, in terms of high quantity, thus preventing early decomposition of the briquettes. In the case of barbeque coal, the starch addition amounts to between 4 and 6%, in the case of calorized coal to between 0.1 and 0.5%. Moreover, starches are gaining importance as binders since the emission of noxious substances can be markedly reduced when starches are added to coal and briquettes.

2.9. Ore Slick and Coal Silt Preparation

Furthermore, starch can be employed as flocculant in the ore slick and coal silt preparation.

2.10. Foundry Auxiliary

A further field of application is as an additive to foundry auxiliaries. Various casting processes require cores made with sands treated with binders. The binder which is predominantly employed nowadays is bentonite, which is treated with modified starches, in most cases swellable starches. The purpose of adding starch is to increase flowability and to improve the binding power. In addition, the swellable starches can meet other demands of production engineering, such as being cold-water-dispersible, rehydratable and readily miscible with sand and having high water binding capacity.

2.11. Use in the Rubber Industry

In the rubber industry, starch is employed for improving the technical and visual quality. The reasons are the improvement of the surface luster, the improvement of handle and of appearance, and to this end starch is scattered to the tacky gummed surfaces of rubber materials prior to cold curing, and also the improvement of the rubber's printability.

2.12. Production of Leather Substitutes

Modified starches may furthermore also be sold for the production of leather substitutes.

2.13. Starch in Synthetic Polymers

In the polymer sector, the following fields of application can be envisaged: the use of starch degradation products in the processing process (the starch is only a filler, there is no direct bond between the synthetic polymer and the starch) or, alternatively, the use of starch degradation products in the production of polymers (starch and polymer form a stable bond).

The use of starch as a pure filler is not competitive in comparison with other substances such as talc. However, this is different when the specific properties of starch make an impact and thus markedly alter the spectrum of characteristics of the end products. An example of this is the use of starch products in the processing of thermoplastics, such as polyethylene. Here, the starch and the synthetic polymer are combined by coexpression in a ratio of 1:1 to give a masterbatch, from which various products are produced together with granulated polyethylene, using conventional process techniques. By using starch in polyethylene films, an increased substance permeability in the case of hollow bodies, an improved permeability for water vapor, an improved antistatic behavior, an improved antiblock behavior and an improved printability with aqueous inks can be achieved. The current disadvantages relate to the insufficient transparency, the reduced tensile strength and a reduced elasticity.

Another possibility is the use of starch in polyurethane foams. By adapting the starch derivatives and by process-engineering optimization, it is possible to control the reaction between synthetic polymers and the starches' hydroxyl groups in a directed manner. This results in polyurethane films which have the following spectrum of properties, owing to the use of starch: a reduced heat extension coefficient, a reduced shrinking behavior, an improved pressure-tension behavior, an increase in permeability for water vapor without altering the uptake of water, a reduced flammability and a reduced ultimate tensile strength, no drop formation of combustible parts, freedom from halogens and reduced aging. Disadvantages which still exist are a reduced printability and a reduced impact strength.

Product development is currently no longer restricted to films. Solid polymer products such as pots, slabs and dishes which contain a starch content of over 50% may also be prepared. Moreover, starch/polymer mixtures are considered advantageous since their biodegradability is much higher.

Starch graft polymers have become exceedingly important owing to their extremely high water binding capacity. They are products with a starch backbone and a side chain of a synthetic monomer, grafted on following the principle of the free-radical chain mechanism. The currently available starch graft polymers are distinguished by a better binding and retention capacity of up to 1000 g of water per g of starch combined with high viscosity. The fields of application for these superabsorbers have extended greatly in recent years and are, in the hygiene sector, the products diapers and pads and, in the agricultural sector, for example seed coatings.

What is decisive for the application of novel, genetically engineered starches are, on the one hand, structure, water content, protein content, lipid content, fiber content, ash/phosphate content, amylose/amylopectin ratio, molecular mass distribution, degree of branching, granule size and granule shape and crystallization, and, on the other hand, also the characteristics which affect the following features: flowing and sorption behavior, gelatinization temperature, viscosity, thickening power, solubility, gel structure, transparency, heat stability, shear stability, stability to acids, tendency to undergo retrogradation, gel formation, freeze-thaw stability, complex formation, iodine binding, film formation, adhesive power, enzyme stability, digestibility and reactivity.

The production of modified starches by means of genetic engineering methods can, on the one hand, alter the properties, for example of the starch derived from the plant in such a way that other modifications by means of chemical or physical alterations are no longer required. On the other hand, starches which have been altered by genetic engineering methods may be subjected to further chemical modification, which leads to further improvements in quality for some of the above-described fields of application. These chemical modifications are known in principle. They are, in particular, modifications by heat and pressure treatment, treatment with organic or inorganic acids, enzymatic treatment, oxidations or esterifications, which lead, for example, to the formation of phosphate starches, nitrate starches, sulfate starches, xanthate starches, acetate starches and citrate starches. Moreover, mono- or polyhydric alcohols in the presence of strong acids may be employed for preparing starch ethers, resulting in starch alkyl ethers, o-allyl ethers, hydroxyalkyl ethers, O-carboxylmethyl ethers, N-containing starch ethers, P-containing starch ethers, S-containing starch ethers, crosslinked starches or starch graft polymers.

A use of the starches according to the invention is in industrial application, preferably for foodstuffs or the preparation of packaging materials and disposable articles.

The examples which follow serve to illustrate the invention and constitute in no way a restriction.

Abbreviations:

| | |
|---|---|
| BE | branching enzyme |
| bp | base pair |
| GBSS | granule bound starch synthase |
| IPTG | isopropyl-β-D-thiogalactopyranoside |
| SS | soluble starch synthase |
| PMSF | phenylmethylsulfonyl fluoride |

Media and solutions used in the examples:

| | |
|---|---|
| 20 × SSC | 175.3 g NaCl; 88.2 g sodium citrate to 1000 ml with double-distilled H$_2$O pH 7.0 with 10 N NaOH |
| Buffer A | 50 mM Tris-HCl pH 8.0; 2.5 mM DTT; 2 mM EDTA; 0.4 mM PMSF; 10% glycerol; 0.1% sodium dithionite |
| Buffer B | 50 mM Tris-HCl pH 7.6; 2.5 mM DTT; 2 mM EDTA |
| Buffer C | 0.5 M sodium citrate pH 7.6; 50 mM Tris-HCl pH 7.6; 2.5 mM DTT 2 mM EDTA |
| 10 × TBS | 0.2 M Tris-HCl pH 7.5; 5.0 M NaCl |
| 10 × TBST | 10 × TBS; 0.1% (v/v) Tween 20 |
| Elution buffer | 25 mM Tris pH 8.3; 250 mM glycine |
| Dialysis buffer | 50 mM Tris-HCl pH 7.0; 50 mM NaCl; 2 mM EDTA; 14.7 mM beta-mercaptoethanol; 0.5 mM PMSF |
| Protein buffer | 50 mM sodium phosphate buffer pH 7.2; 10 mM EDTA; 0.5 mM PMSF; 14.7 mM beta-mercaptoethanol |

BRIEF DESCRIPTION OF THE FIGURES

FIG. 1 represents a schematic RVA temperature profile (viscosity and temperature vs. Time [min]), this with the viscosimetric parameters T=gelatinization temperature, temperature at the beginning of gelatinization; Max specifies the maximum viscosity; Min specifies the minimum viscosity; Fin specifies the viscosity at the end of the measurement; Set is the difference (D) of Min and Fin (setback).

FIG. 2A-2B shows the side-chain distribution of the amylopectin samples determined on the right by means of HPAEC-PAC (voltage [mV] vs. Time [min]) and, on the left, determined by gel permeation chromatography (current [nC] vs. Time [min]). A=control (wild-type No. 1); B= (asSSII, No. 7); C=(asSSIII, No. 8); D=(asSSII asSSIII, No. 13); E=(asSSII asSSIII, No. 14).

Figure 2A:
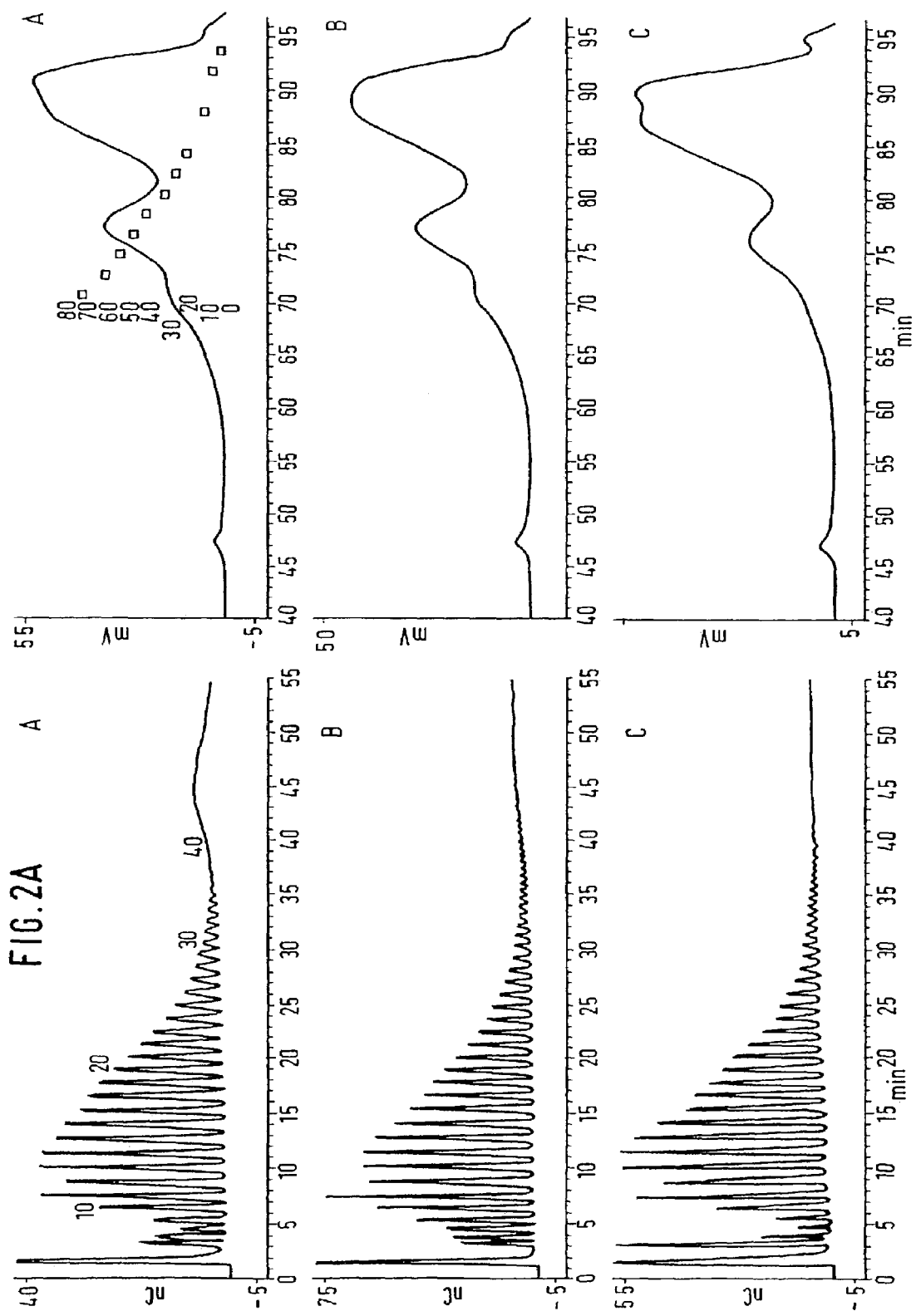

The numbers given in brackets in the description of the figures relate to the numbers of the starch samples described in Tables 1 and 2.

The following methods were used in the examples:

1. Cloning Method

The vector pBluescript II SK (Stratagene) was used for cloning into *E.coli*

For the transformation of plants, the gene constructions were cloned into the binary vector pBinAR Hyg (Höfgen & Willmitzer, 1990, Plant Sci. 66:221-230) and pBinB33-Hyg.

2. Bacterial Strains and Plasmids

The *E. coli* strain DH5a (Bethesda Research Laboratories, Gaithersburgh, USA) was used for the Bluescript vector p Bluescript II KS (Stratagene) and for the pBinAR Hyg and pBinB33 Hyg constructs. The *E. coli* strain XL1-Blue was used for the in vivo excision.

pBinAR

The plasmid pBinAR is a derivative of the binary vector plasmid pBin19 (Bevan, 1984), which was constructed as follows:

A 529 bp fragment encompassing the nucleotides 6909-7437 of the cauliflower mosaic virus 35S promoter was isolated from plasmid pDH51 as an EcoRI/KpnI fragment (Pietrzak et al., 1986), ligated between the EcoRI and KpnI cleavage sites of the pUC18 polylinker and was termed plasmid pUC18-35S. With the aid of the restriction endonucleases HindIII and PvuII, a 192 bp fragment was isolated from plasmid pAGV40 (Herrera-Estrella et al., 1983), which encompasses DNA of the Ti plasmid pTiACH5 (Gielen et al, 1984) (nucleotides 11749-11939). After the PvuII cleavage site had been provided with SphI linkers, the fragment was ligated between the SphI and HindIII cleavage sites of pUC18-35S, and this was termed plasmid pA7. Moreover, the entire polylinker comprising the 35S promoter and the ocs terminator was excised with EcoRI and HindIII and ligated into the suitably cleaved pBin19. This gave rise to the plant expression vector pBinAR (Höfgen and Willmitzer, 1990).

pBinB33

The promoter of the *Solanum tuberosum* patatin gene B33 (Rocha-Sosa et al., 1989) was ligated, as a DraI fragment (nucleotides-1512-+14) into the Sst I-cleaved vector PUC19, which had been made blunt-ended with the aid of T4-DNA polymerase. This gave rise to the plasmid pUC19-B33. The B33 promoter was excised from this plasmid with EcoRI and SmaI and ligated into the suitably cleaved vector pBinAR. This gave rise to the plant expression vector pBinB33.

pBinAR-Hyg

Starting from plasmid pA7 (cf. description of vector pBinAR), the EcoRI-HindIII fragment comprising the 35S promoter, the ocs terminator and the polylinker portion between 35S promoter and ocs terminator was introduced into the suitably cleaved plasmid pBin-Hyg.

pBinB33-Hyg

Starting from plasmid pBinB33, the EcoRI-HindIII fragment comprising the B33 promoter, part of the polylinker and the ocs terminator was cleaved out and ligated into the suitably cleaved vector pBin-Hyg. This gave rise to the plant expression vector pBinB33-Hyg.

3. Transformation of *Agrobacterium tumefaciens*

The DNA was transferred by direct transformation following the method of Höfgen&Willmitzer (1988, Nucleic Acids Res. 16:9877). The plasmid DNA of transformed *agrobacteria* was isolated following the method of Bimboim&Doly (1979, Nucleic Acids Res. 7:1513-1523), subjected to suitable restriction cleavage, and then analyzed by gel electrophoresis.

4. Transformation of Potatoes

The plasmids were transformed into the potato plants (*Solanum tuberosum* L. cv. Desiree, Vereinigte Saatzuchten eG, Ebstorf) with the aid of the *Agrobacterium tumefaciens* strain C58C1 (Dietze et al. (1995) in Gene Transfer to Plants. pp. 24-29, eds.: Potrykus, I. and Spangenberg, G., Springer Verlag, Deblaere et al., 1985, Nucl. Acids Res. 13:4777-4788).

Ten small leaves of a sterile potato culture which had been wounded with a scalpel were placed into 10 ml MS medium (Murashige&Skoog (1962) Physiol. Plant. 15: 473) supplemented with 2% sucrose and containing 50 ml of an *Agrobacterium tumefaciens* overnight culture grown under selection conditions. After the culture had been shaken gently for 3-5 minutes, it was incubated for 2 more days in the dark. For callus induction, the leaves were then placed on MS medium supplemented with 1.6% glucose, 5 mg/l naphthylacetic acid, 0.2 mg/l benzylaminopurine, 250 mg/l claforan, 50 mg/l canamycin, and 0.80% Bacto agar. After the leaves had been incubated for one week at 25 C and 3000 Lux, they were placed on MS medium supplemented with 1.6% glucose, 1.4 mg/l zeatin ribose, 20 mg/l naphthylacetic acid, 20 mg/l gibberellic acid, 250 mg/l claforan, 50 mg/l canamycin, and 0.80.% Bacto agar, to induce shoots.

5. Plant Culture Regime

Potato plants were kept in the greenhouse under the following regime:

| | |
|---|---|
| Light period | 16 h at 25,000 Lux and 22° C. |
| Dark period | 8 hours at 15° C. |
| Atmospheric humidity | 60% |

6. Radiolabeling of DNA Fragments

The DNA fragments were radiolabeled with the aid of a DNA Random Primer Labeling Kit by Boehringer Mannheim (Germany) following the manufacturer's instructions.

7. Determination of Starch Synthase Activity

Determination of starch synthase activity was done by determining the incorporation of $^{14}$C Glucose from ADP [$^{14}$C glucose] into a methanol/KCl-insoluble product as described by Denyer & Smith, 1992, Planta 186:609-617.

8. Detection of Soluble Starch Synthases in the Native Gel

To detect the activity of soluble starch synthases by non-denaturing gel electrophoresis, tissue samples of potato tubers were hydrolyzed in 50 mM Tris-HCl pH 7.6, 2 mM DTT, 2.5 mM EDTA, 10% glycerol and 0.4 mM PMSF. The electrophoresis was carried out in a MiniProtean II chamber (BioRAD). The monomer concentration of the 1.5-mm-thick gels was 7.5% (w/v), and 25 mM Tris-glycine pH 8.4 was used as gel buffer and running buffer. Identical amounts of protein extract were applied and separated for 2 hours at 10 mA per gel.

The activity gels were subsequently incubated in 50 mM Tricine-NaOH pH 8.5, 25 mM potassium acetate, 2 mM EDTA, 2 mM DTT, 1 mM ADP-glucose, 0.1% (w/v) amylopectin and 0.5 M sodium citrate. The glucans formed were stained with Lugol's solution.

9. Starch Analysis

The starch formed by the transgenic potato plants was characterized by the following methods:

a) Determination of the Amylose/Amylopectin Ratio in Starch from Potato Plants

Starch was isolated from potato plants by standard methods, and the amylose:amylopectin ratio was determined by the method described by Hovenkamp-Hermelink et al.(Potato Research 31 (1988) 241-246).

b) Determination of the Phosphate Content

In potato starch, some glucose units may be phosphorylated on the carbon atoms at positions C2, C3 and C6. To determine the degree of phosphorylation at the C6-position of the glucose, 100 mg of starch were hydrolyzed for 4 hours at 95° C. in 1 ml of 0.7 M HCl (Nielsen et. al. (1994) Plant Physiol. 105: 111-117). After neutralization with 0.7 M KOH, 50 ml of the hydrolysate were subjected to a visual-enzymatic test to determine glucose-6-phosphate. The change in absorption of the test batch (100 mM imidazole/HCl; 10 mM $MgCl_2$; 0.4 mM NAD; 2 units of *Leuconostoc mesenteroides*, glucose-6-phosphate dehydrogenase; 30° C.) was monitored at 334 nm. The total phosphate was determined as described by Ames, 1996, Methods in Enzymology VIII, 115-118.

c) Analysis of the Amylopectin Side Chains

To analyze distribution and length of the side chains in the starch samples, 1 ml of a 0.1% starch solution was digested with 0.4 U of isoamylase (Megazyme International Ireland Ltd., Bray, Ireland) overnight at 37 C in 100 mM sodium citrate buffer, pH 3.5.

The rest of the analysis was carried out as described by Tomlinson et al., (1997), Plant J. 11:31-47, unless otherwise specified.

d) Granule Size Determination

The granule size was determined using a "Lumosed" photosedimentometer by Retsch GmbH, Germany. To this end, 0.2 g of starch were suspended in approx. 150 ml of water and immediately measured. The program supplied by the manufacturer calculated the mean diameter of the starch granules, assuming an average starch density of 1.5 g/l.

e) Gelatinization Properties

The gelatinization or viscosity properties of the starch were recorded using a Viskograph E by Brabender OHG, Germany, or using a Rapid Visco Analyzer, Newport Scientific Pty Ltd, Investment Support Group, Warriewood NSW 2102, Australia. When using the Viskograph E, a suspension of 20 g of starch in 450 ml of water was subjected to the following heating program: heating at 3°/min from 50° C. to 96° C., keep constant for 30 minutes, cool at 3°/min to 30° C., and again keep constant for 30 minutes. The temperature profile gave characteristic gelatinization properties.

When measuring using the Rapid Visco Analyzer (RVA), a suspension of 2 g of starch in 25 ml of water was subjected to the following heating program: suspend for 60 seconds at 50° C., heat at 12°/min from 50° C. to 95° C., keep constant for 2.5 minutes, cool at 12° C./min to 50° C., and again keep constant for 2 minutes. The RVA temperature profile gave the viscometric parameters of the test starches for the maximum viscosity (Max), the end viscosity (Fin), the gelatinization temperature (T), the minimum viscosity occurring after the maximum viscosity (Min), and the difference between minimum and end viscosity (setback, Set) (cf. Table 1 and FIG. 1).

f) Determination of the Gel Strength

To determine the gel strength by means of a Texture Analyzer, 2 g of starch were gelatinized in 25 ml of water (cf. RVA measurement) and then stored for 24 hours in a sealed container at 25° C. with the exclusion of air. The samples were mounted underneath the probe (circular stamp) of a Texture Analyzer TA-XT2 (Stable Micro Systems), and the gel strength was determined with the following parameter settings:

| Test speed | 0.5 mm |
| Penetration depth | 7 mm |
| Contact area (of the stamp) | 113 $mm^2$ |
| Pressure/contact area | 2 g |

10. Determination of Glucose, Fructose and Sucrose

To determine the glucose, fructose and sucrose content, small tuber portions (approx. diameter 10 mm) of potato tubers were frozen in liquid nitrogen and then extracted for 30 minutes at 80° C. in 0.5 ml of 10 mM HEPES, pH 7.5; 80% (vol./vol.) ethanol. The supernatant, which contains the solubles: was removed and the volume was determined. The supernatant was used for determining the amount of soluble sugars. The quantitative determination of soluble glucose, fructose and sucrose was carried out in a batch with the following composition

| 100.0 | mM imidazole/HCl, pH 6.9 |
| 1.5 | mM $MgCl_2$ |
| 0.5 | mM $NADP^+$ |
| 1.3 | mM ATP |
| 10–50 | μl sample |
| 1.0 | unit yeast glucose-6-phosphate dehydrogenase |

The batch was incubated for 5 minutes at room temperature. The sugars were subsequently determined photometrically by measuring the absorption at 340 nm after the successive addition of

| 1.0 | unit yeast hexokinase (to determine glucose), |
| 1.0 | unit yeast phosphoglucoisomerase (to determine fructose) and |
| 1.0 | unit yeast invertase (to determine sucrose) |

To determine the water uptake capacity, the solubles of the starch which had swelled at 70° C. were removed by centrifugation (10 min at 10,000× g) and the residue was then weighed. The water uptake capacity of the starch was based on the initial starch quantity corrected by the soluble matter.

$WUC(g/g)$=(residue−(initial quantity−solubles))/(initial quantity−solubles)

EXAMPLES

Example 1

Preparation of Plasmid p35SαSSI-Hyg

A 1831 bp Asp718/XbaI fragment containing a partial cDNA encoding the potato SS I (Abel, G., (1995), PhD thesis, Freie Universität Berlin) was introduced between the Asp718 and XbaI cleavage site of the vector pBinAR-Hyg in antisense orientation relative to the 35S promoter.

Example 2

Preparation of Plasmid p35S-SSI-Kan

A 2384 bp EcoRI fragment containing cDNA encoding potato SS I (Abel 1995, loc.cit.) was made blunt-ended and introduced into the vector pBinAR, which had previously been cut with SmaI, in sense orientation relative to the 35S promoter.

Example 3

Preparation of Plasmid p35SαSSII-Kan

A 1959 bp SmaI/Asp718 fragment containing a partial cDNA encoding potato SS II (Abel, 1995, termed GBSS II therein) was made blunt-ended and introduced into the SmaI cleavage site of the vector pBinAR in antisense orientation relative to the 35S promoter.

Example 4

Preparation of plasmid pB33-SSII-Hyg

A 2619 bp SmaI/SalI fragment containing a cDNA encoding the potato SS II (Abel, 1995, loc.cit.) was introduced into the vector pBinB33-Hyg, which had previously been cut with SmaI and SalI in sense orientation relative to the B33 promoter.

Example 5

Preparation of Plasmid p35SαSSIII-Hyg

A 4212 bp Asp718/XbaI fragment containing a cDNA encoding the potato SS III (Abel et al., 1996, Plant J. 10(6):981-991) was inserted between the Asp718 and the XbaI cleavage site of the vector pBinAR-Hyg in antisense orientation relative to the 35S promoter.

Example 6

Preparation of Plasmid p35S-SSIII-Kan

A 4191 bp EcoRI fragment containing a cDNA encoding the potato SS III (Abel et al., 1996, loc.cit.) was made blunt-ended and introduced into the SmaI cleavage site of the vector pBinAR in sense orientation relative to the 35S promoter.

Example 7

Preparation of Plasmid pB33αBEαSSIII-Kan

A 1650 bp HindII fragment which contains a partial cDNA encoding the potato BE enzyme (Kossmann et al., 1991, Mol. & Gen. Genetics 230(1-2):39-44) was made blunt-ended and introduced into the vector pBinB33 which had been precut with SmaI in antisense orientation relative to the B33 promoter. The resulting plasmid was cut open with BamHI. A 1362 bp BamHI fragment containing a partial cDNA encoding the potato SS III enzyme (Abel et al., 1996, loc.cit.) was introduced into the cleavage site, again in antisense orientation relative to the B33 promoter.

Example 8

Preparation of Plasmid p35SαSSII-αSSIII-Kan

A 1546 bp EcoRV/HincII fragment containing a partial cDNA encoding for the potato SS II (Abel, 1995, loc.cit.) was cloned into the vector pBluescript II KS which had been cut with EcoRV/HincII, then excised via an Asp718/BamHI digest and introduced in antisense orientation relative to the 35S promoter into the vector pBinAR which had been digested in the same manner. Then, a 1356 bp BamHI fragment containing a partial cDNA encoding the potato SS III (Abel et al., 1996, loc.cit.) was introduced into the BamHI cleavage site of the vector pBinAR-SSII, again in antisense orientation relative to the 35S promoter.

Example 9

Preparation of Plasmid pB33αSSIαSSIII-Kan

A 2384 bp EcoRI fragment containing a cDNA encoding the potato SS I (Abel, 1995, loc.cit.) was made blunt-ended and cloned into the SmaI-cleavage site of the pBinB33 vector in antisense orientation relative to the B33 promoter. A 1362 bp BamHI fragment containing a partial cDNA encoding the potato SS III (Abel et al., 1996, loc.cit.) was introduced into the BamHI cleavage site of the resulting vector, again in antisense orientation relative to the B33 promoter.

Example 10

Preparation of Plasmid p35SαSSII-Hyg

A 1959 bp SmaI/Asp718 fragment containing a partial cDNA encoding for the SS II (Abel, 1995, loc.cit.) was made blunt-ended and introduced into the SmaI cleavage site of the pBinAR-Hyg vector in antisense orientation relative to the 35S promoter.

Example 10B

Preparation of Plasmid pB33αR1-Hyg

A 1.9 kB Asp718 fragment containing a partial cDNA encoding R1 protein derived from *s. tuberosum* (WO 97/11188) was obtained from the vector pBluescript. The fragment was cloned into the Asp718 restriction site after the B33 promoter in anti-sense orientation relative to the vector pB33-Binar-Hyg comprising hygromycin resistance.

Example 11

Introduction of the Plasmids into the Genome of Potato Cells

The plasmids given in Examples 1 to 10 were transferred into *agrobacteria*, either individually and/or in succession, with the aid of which potato cells were transformed as described above. Subsequently, entire plants were regenerated from the transformed plant cells.

Transgenic plant cells of the genotype asSSI-asSSII-asSSIII were generated by transformation with the plasmid p35SαSSI-Hyg described in Ex. No. 1 and subsequent retransformation with the plasmid p35SαSSII-αSSIII-Kan described in Ex. No. 8.

Transgenic plant cells of the genotype asSSII-aSSI-asSSIII were generated by transformation with the plasmid p35SαSSII-Hyg described in Ex. No. 10 and subsequent retransformation with the plasmid pB33αSSIαSSIII-Kan described in Ex. No. 9.

As a result of the transformation, the transgenic potato plants synthesized altered starch varieties.

Example 12

Physico-Chemical Characterization of the Modified Starches

The starch formed by the transgenic plants generated in accordance with Example 11 differs, for example, from starch synthesized by wild-type plants (potato) with regard to its phosphate or amylose content and the viscosities and gelatinization properties which were determined by RVA. The results of the physico-chemical characterization of the modified starches are shown in Table 1. In the antisense constructs, the enzyme activities of the suppressed soluble starch synthases were reduced by up to 85% relative to the untransformed control plants.

Example 13

Characterization of the Side Chains of the Modified Starches

The glucan chains were separated after removing the amylose by means of thymol precipitation (Tomlinson et al. loc. cit.) using a high performance anion exchanger chromatography system with an amperometric detector (HPEAC-PAD, Dionex). The samples (10 mg/ml amylopectin) were dissolved in 40% DMSO and ⅒ part by volume of 100 mM sodium acetate pH 3.5 and 0.4 U of isoamylase (Megazyme) were added. After incubation, 10 μl of the sample were applied to the column system and eluted as described by Tomlinson et al. (loc. cit.).

TABLE 1

Properties of the modified starches

| No. | Genotype | Phosphate (%) | Amylose (%) | RVA Max (%) | RVA Min (%) | RVA Fin (%) | RVA Set (%) | RVA T (%) | Gel strength (%) |
|---|---|---|---|---|---|---|---|---|---|
| 1 | Désirée (wild type) | 100 | 100 | 100 | 100 | 100 | 100 | 100 | 100 |
| 2 | asSSI | 100 | 100 | 113 | 100 | 100 | 114 | 100 | 112 |
| 3 | oeSSI | 140 | 100 | 118 | 152 | 111 | 45 | 100 | 106 |
| 4 | oeSSI | 91 | 100 | 87 | 178 | 131 | 55 | 100 | 335 |
| 5 | oeSSI | 127 | 100 | 100 | 157 | 121 | 63 | 100 | 313 |
| 6 | cosSSI | 100 | 100 | 106 | 100 | 100 | 100 | 100 | 127 |
| 7 | asSSII | 55 | 118 | 76 | 91 | 95 | 113 | 98 | 151 |
| 8 | asSSIII | 197 | 123 | 82 | 75 | 76 | 79 | 95 | 84 |
| 9 | oeSSIII | 100 | | 100 | 100 | 88 | 87 | 100 | 68 |
| 10 | cosSSIII | 210 | | 100 | 60 | 70 | 74 | 95 | 83 |
| 11 | asBE | 170 | 91 | 124 | 94 | 90 | 76 | 100 | 91 |
| 12 | asBE-asSSIII | 292 | | 128 | 69 | 75 | 97 | 95 | 100 |
| 13 | asSSII-asSSIII | 31 | 124 | 30 | 77 | 107 | 229 | 93 | 212 |
| 14 | asSSII-asSSIII | 39 | 110 | 45 | 88 | 113 | 216 | 94 | 189 |
| 15 | asSSI-asSSIII | 115 | | | | | | | |
| 15b | asSSI-asSSIII | 86 | 100 | 82 | 74 | 96 | 168 | 100 | 100 |
| 16 | asSSII-asSSIII-asSSI | | | | | | | | |
| 17 | asSSI-asSSII-asSSIII | 54 | 115 | 60 | 141 | 105 | 133 | 97 | 105 |
| 18 | asSSII-asSSI-asSSIII | | | | | | | | |
| 19 | asBE-asSSIII-oeSSI | 370 | 85 | 131 | 55 | 60 | 84 | 93 | 66 |
| 20 | asBE-asSSIII-asR1 | 125 | 136 | | | | | | |
| 21 | oeSSIII-oeSSII | 105 | 100 | 127 | 122 | 126 | 136 | 94 | 189 |

Key:
SSI = starch synthase isoform I;
SSII = starch synthase isoform II;
SSIII = starch synthase isoform III;
BE = branching enzyme;
as = antisense;
oe = overexpressed (sense);
cos = cosuppressed (sense);
Rapid Visco Analyzer - (RVA) data:
Max = maximum viscosity;
Min = minimum viscosity;
Fin = viscosity at the end of the measurement;
Set is the difference (D) of Min and Fin (setback);
T = gelatinization temperature
The percentages are based on the wild type (=100%).

The results of the HPEAC-PAD analysis regarding length and distribution of the side chains of the starch samples Nos. 1, 7, 8, 13 and 14 (cf.Tables1 and 2) are shown in FIG. 2.

Another HPLC system for detecting the side-chain distribution consisted of 3 columns connected in series (2 TSK-Gel 2000SW and one TSK-Gel 3000SW, TosoHaas, Stuttgart, Germany) as described by Hizukuri ((1986) Carbohydr. Res. 147:342-347). 100 µl of the prepared sample were applied to the column system. The eluent used was 10 mM sodium acetate pH 3.0 at a flow rate of 0.35 ml/min. The glucans were detected by means of a refraction index detector (Gynkotek), and the chain lengths of the eluted linear glucans were determined by mass spectrometry and iodometry (Hizukuri (1986) loc.cit.).

The results of the gel-chromatographic HPLC analysis regarding length and distribution of the side chains of starch samples Nos. 1, 7, 8, 13 and 14 (cf. Tables 1 and 2) are shown in FIG. 2.

Table 2 shows the percentages of various side-chain fractions of the starches which have been analyzed. Fraction 1 represents the percentage of the A and B1 chains (Hizukuri (1986) loc.cit.), Fraction 2 represents the percentage of the B2, B3 and B4 chains (Hizukuri (1986) loc.cit.) and Fraction 3 shows the percentage of the high-molecular glucan molecules which elute in the exclusion volume.

TABLE 2

Distribution of the amylopectin side chains of the modified starch

| No. | Genotype | Fraction 1 (%) | Fraction 2 (%) | Fraction 3 (%) |
|---|---|---|---|---|
| 1 | Désirée (wild type) | 58.7 | 40.3 | 1.0 |
| 7 | asSSII | 62.6 | 36.5 | 0.9 |
| 8 | asSSIII | 72.4 | 26.3 | 1.3 |
| 13 | asSSIIasSSIII | 66.9 | 27.5 | 5.6 |
| 14 | asSSIIasSSIII | 61.5 | 35.1 | 3.4 |

The invention claimed is:

1. An isolated recombinant nucleic acid molecule comprising:
   (a) at least one fragment of a sequence encoding a potato soluble starch synthase III; and
   (b) at least one fragment of a sequence encoding a potato branching enzyme, wherein the fragments are at least 500 nucleotides in length, and wherein the nucleic acid molecule inhibits synthesis of endogenous soluble starch synthase III and endogenous branching enzyme when introduced into plants.

2. The nucleic acid molecule of claim 1, which is a deoxyribonucleic acid molecule.

3. The nucleic acid molecule of claim 1, which is a ribonucleic acid molecule.

4. The nucleic acid molecule of claim 1, wherein the synthesis of endogenous soluble starch synthase III and endogenous branching enzyme is inhibited by cosuppression.

5. The nucleic acid molecule of claim 1, wherein the synthesis of endogenous soluble starch synthase III and endogenous branching enzyme is inhibited by antisense.

6. A vector comprising the nucleic acid molecule of claim 1.

7. The vector according to claim 6, wherein the nucleotide sequence encoding the fragment of a potato soluble starch synthase III is present in antisense orientation.

8. The vector according to claim 6, wherein the nucleotide sequence encoding the fragment of a potato branching enzyme is present in antisense orientation.

9. The vector according to claim 6, wherein the nucleotide sequence encoding the fragment of a potato soluble starch synthase III is present in sense orientation.

10. The vector according to claim 6, wherein the nucleotide sequence encoding the fragment of a potato branching enzyme is present in sense orientation.

11. The vector according to claim 6, wherein the nucleic acid molecule is linked to one or more regulatory elements which ensure transcription and synthesis of an RNA in a eukaryotic cell.

12. A transgenic plant cell, comprising the nucleic acid molecule of claim 1, wherein the plant cell is a potato plant cell.

13. A method of generating a transgenic potato plant which synthesizes a modified starch, comprising regenerating an entire plant from the plant cell of claim 12.

14. A transgenic potato plant obtained by the method of claim 13.

15. Propagation material of the plant of claim 14, wherein the propagation material contains the plant cell.

16. A method for the preparation of a transgenic plant cell comprising transfecting the plant cell with the nucleic molecule of claim 1, wherein the plant cell is a potato plant cell.

17. A method of generating a transgenic plant cell comprising simultaneously or subsequently integrating into the genome of said plant cell:
   (a) at least one fragment of a sequence encoding a potato soluble starch synthase III; and
   (b) at least one fragment of a sequence encoding a potato branching enzyme thereby inhibiting the synthesis of endogenous soluble starch synthase III and endogenous branching enzyme,
   wherein the plant cell is a potato plant cell, and
   wherein said fragments are at least 500 nucleotides in length.

18. A method for inhibiting synthesis of endogenous soluble starch synthase III and endogenous branching enzyme in a potato plant comprising transforming the plant with the nucleic acid molecule of claim 1, whereby the synthesis of endogenous soluble starch synthase III and endogenous branching enzyme is inhibited by cosuppression or antisense.

19. A method for producing starch comprising obtaining starch from the plant cell of claim 12.

20. A method for producing starch comprising obtaining starch from the plant of claim 14.

21. A method for producing starch comprising obtaining starch from the propagation material of claim 15.

22. The nucleic acid molecule of claim 1, wherein the potato branching enzyme is the potato branching enzyme I (BE I).

23. The method of claim 17, wherein the potato branching enzyme is the potato branching enzyme I (BE I).

* * * * *

SEQUENCE LISTING

<160> NUMBER OF SEQ ID NOS: 1

<210> SEQ ID NO 1
<211> LENGTH: 3693
<212> TYPE: DNA
<213> ORGANISM: Solanum tuberosum

<400> SEQUENCE: 1

```
atggatgttc catttccact gcatagacca ttgagttgca caagtgtctc caatgcaata      60
acccacctca agatcaaacc ttttcttggg tttgtctctc atggaaccac aagtctatca     120
gtacaatctt cttcatggag gaaggatgga atggttactg gggtttcatt tccattttgt     180
gcaaatctct cgggaagaag acggagaaaa gtttcaacta ctaggagtca aggatcttca     240
cctaaggggt ttgtgccaag gaagccctca gggatgagca cgcaaagaaa ggttcagaag     300
agcaatggtg ataaagaaag tcaaagtact tcaacatcta aagaatctga aatttccaac     360
cagaagacgg ttgaagcaag agttgaaact agtgacgatg acactaaagt agtggtgagg     420
gaccacaagt ttctggagga tgaggatgaa atcaatggtt ctactaaatc aataagtatg     480
tcacctgttc gtgtatcatc tcaatttgtt gaaagtgaag aaactggtgg tgatgacaag     540
gatgctgtaa agttaaacaa atcaaagaga tcggaagaga gtgattttct aattgattct     600
gtaataagag aacaaagtgg atctcagggg gaaactaatg ccagtagcaa gggaagccat     660
gctgtgggta caaaacttta tgagatattg caggtggatg ttgagccaca acaattgaaa     720
gaaaataatg ctgggaatgt tgaatacaaa ggacctgtag caagtaagct attggaaatt     780
actaaggcta gtgatgtgga acacactgaa agcaatgaga ttgatgactt agacactaat     840
agtttcttta aatcagattt aattgaagag gatgagccat tagctgcagg aacagtggag     900
actggagatt cttctctaaa cttaagattg gagatggaag caaatctacg taggcaggct     960
atagaaaggc ttgccgagga aaatttattg caagggatca gattattttg ttttccagag    1020
gttgtaaaac ctgatgaaga tgtcgagata tttcttaaca gaggtctttc cactttgaag    1080
aatgagtctg atgtcttgat tatgggagct tttaatgagt ggcgctatag gtcttttact    1140
acaaggctaa ctgagactca tctcaatgga gattggtggt cttgcaagat ccatgttccc    1200
```

-continued

```
aaggaagcat acagggctga ttttgtgttt tttaatggac aagatgtcta tgacaacaat      1260
gatggaaatg acttcagtat aactgtgaaa ggtggtatgc aaatcattga ctttgaaaat      1320
ttcttgcttg aggagaaatg gagagaacag gagaaacttg ctaaagaaca agctgaaaga      1380
gaaagactag cggaagaaca aagacgaata gaagcagaga aagctgaaat tgaagctgac      1440
agagcacaag caaaggaaga ggctgcaaag aaaaagaaag tattgcgaga attgatggta      1500
aaagccacga agactcgtga tatcacgtgg tacatagagc caagtgaatt taaatgcgag      1560
gacaaggtca ggttatacta taacaaaagt tcaggtcctc tctcccatgc taaggacttg      1620
tggatccacg gaggatataa taattggaag gatggtttgt ctattgtcaa aaagcttgtt      1680
aaatctgaga gaatagatgg tgattggtgg tatacagagg ttgttattcc tgatcaggca      1740
cttttcttgg attgggtttt tgctgatggt ccacccaagc atgccattgc ttatgataac      1800
aatcaccgcc aagacttcca tgccattgtc cccaaccaca ttccggagga attatattgg      1860
gttgaggaag aacatcagat ctttaagaca cttcaggagg agagaaggct tagagaagcg      1920
gctatgcgtg ctaaggttga aaaacagca cttctgaaaa ctgaaacaaa ggaaagaact      1980
atgaaatcat ttttactgtc tcagaagcat gtagtatata ctgagcctct tgatatccaa      2040
gctggaagca gcgtcacagt ttactataat cccgccaata cagtacttaa tggtaaacct      2100
gaaatttggt tcagatgttc atttaatcgc tggactcacc gcctgggtcc attgccacct      2160
cagaaaatgt cgcctgctga aaatggcacc catgtcagag caactgtgaa ggttccattg      2220
gatgcatata tgatggattt tgtattttcc gagagagaag atggtgggat ttttgacaat      2280
aagagcggaa tggactatca cataccgtgt tttggaggag tcgctaaaga acctccaatg      2340
catattgtcc atattgctgt cgaaatggca ccaattgcaa aggtgggagg ccttggtgat      2400
gttgttacta gtctttcccg tgctgttcaa gatttaaacc ataatgtgga tattatctta      2460
cctaagtatg actgtttgaa gatgaataat gtgaaggact tcggttttca caaaaactac      2520
ttttggggtg ggactgaaat aaaagtatgg tttggaaagg tggaaggtct ctcggtctat      2580
tttttggagc ctcaaaacgg gttattttcg aaagggtgcg tctatggttg tagcaatgat      2640
ggtgaacgat ttggttctt ctgtcacgcg gctttggagt ttcttctgca aggtggattt      2700
agtccggata tcattcattg ccatgattgg tctagtgctc ctgttgcttg gctctttaag      2760
gaacaatata cacactatgg tctaagcaaa tctcgtatag tcttcacgat acataatctt      2820
gaatttgggg cagatctcat tgggagagca atgactaacg cagacaaagc tacaacagtt      2880
tcaccaactt actcacagga ggtgtctgga acccctgtaa ttgcgcctca ccttcacaag      2940
ttccatggta tagtgaatgg gattgaccca gatatttggg atcctttaaa cgataagttc      3000
attccgattc cgtacacctc agaaaacgtt gttgaaggca aaacagcagc caaggaagct      3060
ttgcagcgaa aacttggact gaaacaggct gaccttcctt tggtaggaat tatcacccgc      3120
ttaactcacc agaaaggaat ccacctcatt aaacatgcta tttggcgcac cttggaacgg      3180
aacggacagg tagtcttgct tggttctgct cctgatccta gggtacaaaa cgattttgtt      3240
aatttggcaa atcaattgca ctccaaatat aatgaccgcg cacgactctg tctaacatat      3300
gacgagccac tttctcacct gatatatgct ggtgctgatt ttattctagt tccttcaata      3360
tttgagccat gtggactaac acaacttacc gctatgagat atggttcaat tccagtcgtg      3420
cgtaaaactg gaggactttta tgatactgta tttgatgttg accatgacaa agagagagca      3480
caacagtgtg gtcttgaacc aaatggattc agctttgatg gagcagatgc tggcggagtt      3540
gattatgctc tgaatagagc tctctctgct tggtacgatg gtcgggattg gttcaactct      3600
```

```
ttatgcaagc aggtcatgga acaagattgg tcttggaacc gacctgctct tgattatttg    3660
gagctttacc atgctgctag aaagttagaa tag                                 3693
```